(12) United States Patent
Cato

(10) Patent No.: US 11,893,741 B2
(45) Date of Patent: Feb. 6, 2024

(54) SUBPIXEL-BASED IMAGE REGION OF INTEREST RENDERING

(71) Applicant: Fujifilm Medical Systems U.S.A., Inc., Lexington, MA (US)

(72) Inventor: Richard D. Cato, Hillsborough, NC (US)

(73) Assignee: Fujifilm Healthcare Americas Corporation, Lexington, MA (US)

(*) Notice: Subject to any disclaimer, the term of this patent is extended or adjusted under 35 U.S.C. 154(b) by 390 days.

(21) Appl. No.: 17/340,484

(22) Filed: Jun. 7, 2021

(65) Prior Publication Data
US 2022/0392075 A1 Dec. 8, 2022

(51) Int. Cl.
*G06T 7/11* (2017.01)
*G16H 30/40* (2018.01)
*G16H 30/20* (2018.01)

(52) U.S. Cl.
CPC ............... *G06T 7/11* (2017.01); *G16H 30/20* (2018.01); *G16H 30/40* (2018.01); *G06T 2207/30004* (2013.01)

(58) Field of Classification Search
CPC . G06T 7/11; G06T 2207/30004; G16H 30/20; G16H 30/40

USPC .......................................................... 382/128
See application file for complete search history.

(56) References Cited

U.S. PATENT DOCUMENTS

| | | | | |
|---|---|---|---|---|
| 6,166,717 A | * | 12/2000 | Nakayama | G06T 11/203 345/611 |
| 2003/0160980 A1 | * | 8/2003 | Olsson | G03F 7/70291 358/1.9 |
| 2008/0074700 A1 | * | 3/2008 | Olsson | G06T 15/00 358/3.01 |

* cited by examiner

*Primary Examiner* — Michael R Neff
(74) *Attorney, Agent, or Firm* — Baker Botts L.L.P.

(57) ABSTRACT

Computer-implemented method, systems, computer program products include a processor(s) that obtains input data comprising an image and image data: coordinates (points) defining a region of interest in the image. The processor(s) determines a non-duplicative sequential order for navigating the coordinates. The processor(s) defines a set of points bordering the region of interest: points in the image and points comprising intersection points between two coordinates with an edge of a pixel in the image. The processor(s) determines a combined area of sub pixel subregions in each pixel that includes points in the set of points by: identifying the points of the set, generating one or more sub pixel subregions, and utilizing the sub pixel subregions to determine the combined area of sub pixel subregions.

20 Claims, 15 Drawing Sheets

SUBPIXEL-BASED IMAGE REGION OF INTEREST RENDERING

BACKGROUND OF INVENTION

Digital Imaging and Communications in Medicine (DICOM) is the standard for the communication and management of medical imaging information and related data. Regions of interest (ROI) are isolated within DICOM images and from the portion of an image that comprises an ROI, a standard uptake value or standardized uptake value (SUV) can be determined. Accurate isolation of an ROI and the details within this ROI aids in accurate computation of an SUV.

SUMMARY OF INVENTION

Shortcomings of the prior art can be overcome and benefits as described later in this disclosure can be achieved through the provision of a method to identify pixels in a region of interest, including what percentage of each pixel is in the region. Various examples of the system are described below, and the method, including and excluding the additional examples enumerated below, in any combination (provided these combinations are not inconsistent), overcome these shortcomings. The method includes: obtaining, by one or more processors, input data comprising an image and image data comprising coordinates defining a region of interest in the image, wherein each coordinate defines a point on the image, wherein the image comprises pixels; determining, by the one or more processors, a sequential order for navigating the coordinates defining the region of interest, wherein the sequential order is non-duplicative of any coordinate of the coordinates; defining, by the one or more processors, a set of points comprising a border around the region of interest, wherein the defining comprises supplementing the coordinates comprising points in the image by adding additional points comprising intersection points, wherein each intersection point is an intersection of a line between two coordinates of the coordinates with an edge of a pixel of pixels in the image, wherein the coordinates comprising points and the intersection points comprise the set of points; determining, by the one or more processors, a combined area of sub pixel subregions in each pixel comprising one or more points in the set of points, the determining comprising: identifying, by the one or more processors, one or more points of the set of points on the pixel; generating, by the one or more processors, based on the one or more points, one or more sub pixel subregions, wherein each sub pixel subregion comprises contiguous points of the set of points, wherein the contiguous points are within or on the pixel; and utilizing, by the one or more processors, the one or more sub pixel subregions to determine the combined area of sub pixel subregions.

In some examples, the method further comprises, based on the determining the combined area of sub pixel subregions in each pixel, identifying, by the one or more processors, pixels internal the sub pixel subregions.

In some examples, the method further comprises, generating, by the one or more processors, based on determining the combined area of sub pixel subregions in each pixel and the one or more sub pixel subregions of each pixel, a dictionary identifying edge pixels and a percent of each edge pixel of the edge pixels within the region of interest.

In some examples, the method further comprises, generating, by the one or more processors, based on determining the combined area of sub pixel subregions in each pixel and the one or more sub pixel subregions of each pixel, a dictionary comprising a list of the pixels internal to the regions, wherein the pixels internal to the regions are internal to the regions of interest.

In some examples, the image is a Digital Imaging and Communications in Medicine (DICOM) image.

In some examples, the sequential order is selected from the group consisting of: clockwise and counterclockwise.

In some examples, utilizing the one or more sub pixel subregions to determine the combined area of sub pixel subregions for each pixel comprises: generating, by the one or more processors, one or more paths, based on navigating along each edge of the pixel, starting with the edge where a current point is located, in a pre-determined direction, toward a next vertex of the pixel, until each sub pixel subregion is counted, the navigating comprises: determining, by the one or more processors, if any of the sub pixel subregions are uncounted; based on determining that at least one sub pixel subregion is uncounted, generating a path comprising contiguous points comprising the at least one sub pixel subregion, the generating comprising: appending, by the one or more processors, a last coordinate of the uncounted sub pixel subregion to the path, where the last coordinate comprises a current point; determining, by the one or more processors, an edge of the pixel where the current point is located; navigating, by the one or more processors, in the predetermined direction toward the next vertex; based on the navigating, determining, by the one or more processors, if a starting point to a segment of another uncounted sub pixel subregion is on the edge before the next vertex; based on determining that no starting point is on the edge before the vertex, adding coordinates of the next vertex to the path and continuing the navigating in the predetermined direction toward the next vertex; and based on determining that there is a starting point to a segment of another uncounted sub pixel subregion on the edge before the vertex, navigating through the pixel along a segment to an intersection between a point of the contiguous points comprising the other uncounted sub pixel subregion and an edge of the pixel, adding the contiguous points to the path, marking the other uncounted sub pixel subregion as counted, and progressing from the intersection in the pre-determined direction to another vertex.

In some examples, the predetermined direction is selected from the group consisting of: clockwise and counterclockwise.

In some examples, utilizing, the one or more sub pixel subregions to determine the combined area of sub pixel subregions comprises: determining, by the one or more processors, an area for each sub pixel subregion; and adding, by the one or more processors, each determined area together to generate the combined area of sub pixel subregions.

In some examples, the method comprises generating, by the one or more processors, a pixel dictionary; and updating, by the one or more processors, the pixel dictionary to include the set of points, wherein a portion of the set of points comprises edge points.

In some examples, the method comprises generating, by the one or more processors, a dictionary identifying edge pixels, wherein the generating comprises, for each pixel in the region of interest: setting, by the one or more processors, an internal area of the pixel to a constant; determining, by the one or more processors, if a center point of the pixel is within the region of interest; based on determining that the center of the pixel is within the region of interest, determining, by the one or more processors, if the center point is an edge point in the pixel dictionary; based on determining that the center point is the edge point, determining, by the one or more processors, if an edge area of the pixel is greater than zero; and updating, by the one or more processors, the pixel dictionary to include the pixel as an edge pixel.

In some examples, the constant is 1.

Shortcomings of the prior art can be overcome and benefits as described later in this disclosure can be achieved through the provision of a system to identify pixels in a region of interest, including what percentage of each pixel is in the region. Various examples of the system are described below, and the system, including and excluding the additional examples enumerated below, in any combination (provided these combinations are not inconsistent), overcome these shortcomings. The system includes: a memory; one or more processors in communication with the memory; program instructions executable by the one or more processors via the memory to perform a method, the method including: obtaining, by the one or more processors, input data comprising an image and image data comprising coordinates defining a region of interest in the image, wherein each coordinate defines a point on the image, wherein the image comprises pixels; determining, by the one or more processors, a sequential order for navigating the coordinates defining the region of interest, wherein the sequential order is non-duplicative of any coordinate of the coordinates; defining, by the one or more processors, a set of points comprising a border around the region of interest, wherein the defining comprises supplementing the coordinates comprising points in the image by adding additional points comprising intersection points, wherein each intersection point is an intersection of a line between two coordinates of the coordinates with an edge of a pixel of pixels in the image, wherein the coordinates comprising points and the intersection points comprise the set of points; determining, by the one or more processors, a combined area of sub pixel subregions in each pixel comprising one or more points in the set of points, the determining comprising: identifying, by the one or more processors, one or more points of the set of points on the pixel; generating, by the one or more processors, based on the one or more points, one or more sub pixel subregions, wherein each sub pixel subregion comprises contiguous points of the set of points, wherein the contiguous points are within or on the pixel; and utilizing, by the one or more processors, the one or more sub pixel subregions to determine the combined area of sub pixel subregions.

In some examples of the system, the method further comprises, based on the determining the combined area of sub pixel subregions in each pixel, identifying, by the one or more processors, pixels internal the sub pixel subregions.

In some examples of the system, the method further comprises, generating, by the one or more processors, based on determining the combined area of sub pixel subregions in each pixel and the one or more sub pixel subregions of each pixel, a dictionary identifying edge pixels and a percent of each edge pixel of the edge pixels within the region of interest.

In some examples of the system, the method further comprises, generating, by the one or more processors, based on determining the combined area of sub pixel subregions in each pixel and the one or more sub pixel subregions of each pixel, a dictionary comprising a list of the pixels internal to the regions, wherein the pixels internal to the regions are internal to the regions of interest.

In some examples of the system, the image is a Digital Imaging and Communications in Medicine (DICOM) image.

In some examples of the system, the sequential order is selected from the group consisting of: clockwise and counterclockwise.

In some examples of the system, utilizing the one or more sub pixel subregions to determine the combined area of sub pixel subregions for each pixel comprises: generating, by the one or more processors, one or more paths, based on navigating along each edge of the pixel, starting with the edge where a current point is located, in a pre-determined direction, toward a next vertex of the pixel, until each sub pixel subregion is counted, the navigating comprises: determining, by the one or more processors, if any of the sub pixel subregions are uncounted; based on determining that at least one sub pixel subregion is uncounted, generating a path comprising contiguous points comprising the at least one sub pixel subregion, the generating comprising: appending, by the one or more processors, a last coordinate of the uncounted sub pixel subregion to the path, where the last coordinate comprises a current point; determining, by the one or more processors, an edge of the pixel where the current point is located; navigating, by the one or more processors, in the predetermined direction toward the next vertex; based on the navigating, determining, by the one or more processors, if a starting point to a segment of another uncounted sub pixel subregion is on the edge before the next vertex; based on determining that no starting point is on the edge before the vertex, adding coordinates of the next vertex to the path and continuing the navigating in the predetermined direction toward the next vertex; and based on determining that there is a starting point to a segment of another uncounted sub pixel subregion on the edge before the vertex, navigating through the pixel along a segment to an intersection between a point of the contiguous points comprising the other uncounted sub pixel subregion and an edge of the pixel, adding the contiguous points to the path, marking the other uncounted sub pixel subregion as counted, and progressing from the intersection in the pre-determined direction to another vertex.

In some examples of the system, the predetermined direction is selected from the group consisting of: clockwise and counterclockwise.

In some examples of the system, utilizing, the one or more sub pixel subregions to determine the combined area of sub pixel subregions comprises: determining, by the one or more processors, an area for each sub pixel subregion; and adding, by the one or more processors, each determined area together to generate the combined area of sub pixel subregions.

In some examples of the system, the method comprises generating, by the one or more processors, a pixel dictionary; and updating, by the one or more processors, the pixel dictionary to include the set of points, wherein a portion of the set of points comprises edge points.

In some examples of the system, the method comprises generating, by the one or more processors, a dictionary identifying edge pixels, wherein the generating comprises, for each pixel in the region of interest: setting, by the one or more processors, an internal area of the pixel to a constant; determining, by the one or more processors, if a center point of the pixel is within the region of interest; based on determining that the center of the pixel is within the region of interest, determining, by the one or more processors, if the center point is an edge point in the pixel dictionary; based on determining that the center point is the edge point, determining, by the one or more processors, if an edge area of the pixel is greater than zero; and updating, by the one or more processors, the pixel dictionary to include the pixel as an edge pixel.

In some examples of the system, the constant is 1.

Shortcomings of the prior art can be overcome and benefits as described later in this disclosure can be achieved through the provision of a computer program product for identifying pixels in a region of interest, including what percentage of each pixel is in the region. Various examples of the computer program product are described below, and the computer program product, including and excluding the additional examples enumerated below, in any combination (provided these combinations are not inconsistent), overcome these shortcomings. The computer program product includes: a computer readable storage medium readable by one or more processors and storing instructions for execution by the one or more processors for performing a method comprising: obtaining, by the one or more processors, input data comprising an image and image data comprising coordinates defining a region of interest in the image, wherein each coordinate defines a point on the image, wherein the image comprises pixels; determining, by the one or more processors, a sequential order for navigating the coordinates defining the region of interest, wherein the sequential order is non-duplicative of any coordinate of the coordinates; defining, by the one or more processors, a set of points comprising a border around the region of interest, wherein the defining comprises supplementing the coordinates comprising points in the image by adding additional points comprising intersection points, wherein each intersection point is an intersection of a line between two coordinates of the coordinates with an edge of a pixel of pixels in the image, wherein the coordinates comprising points and the intersection points comprise the set of points; determining, by the one or more processors, a combined area of sub pixel subregions in each pixel comprising one or more points in the set of points, the determining comprising: identifying, by the one or more processors, one or more points of the set of points on the pixel; generating, by the one or more processors, based on the one or more points, one or more sub pixel subregions, wherein each sub pixel subregion comprises contiguous points of the set of points, wherein the contiguous points are within or on the pixel; and utilizing, by the one or more processors, the one or more sub pixel subregions to determine the combined area of sub pixel subregions.

In some examples of the computer program product, the method further comprises, based on the determining the combined area of sub pixel subregions in each pixel, identifying, by the one or more processors, pixels internal the sub pixel subregions.

In some examples of the computer program product, the method further comprises, generating, by the one or more processors, based on determining the combined area of sub pixel subregions in each pixel and the one or more sub pixel subregions of each pixel, a dictionary identifying edge pixels and a percent of each edge pixel of the edge pixels within the region of interest.

In some examples of the computer program product, the method further comprises, generating, by the one or more processors, based on determining the combined area of sub pixel subregions in each pixel and the one or more sub pixel subregions of each pixel, a dictionary comprising a list of the pixels internal to the regions, wherein the pixels internal to the regions are internal to the regions of interest.

In some examples of the computer program product, the image is a Digital Imaging and Communications in Medicine (DICOM) image.

In some examples of the computer program product, the sequential order is selected from the group consisting of: clockwise and counterclockwise.

In some examples of the computer program product, utilizing the one or more sub pixel subregions to determine the combined area of sub pixel subregions for each pixel comprises: generating, by the one or more processors, one or more paths, based on navigating along each edge of the pixel, starting with the edge where a current point is located, in a pre-determined direction, toward a next vertex of the pixel, until each sub pixel subregion is counted, the navigating comprises: determining, by the one or more processors, if any of the sub pixel subregions are uncounted; based on determining that at least one sub pixel subregion is uncounted, generating a path comprising contiguous points comprising the at least one sub pixel subregion, the generating comprising: appending, by the one or more processors, a last coordinate of the uncounted sub pixel subregion to the path, where the last coordinate comprises a current point; determining, by the one or more processors, an edge of the pixel where the current point is located; navigating, by the one or more processors, in the predetermined direction toward the next vertex; based on the navigating, determining, by the one or more processors, if a starting point to a segment of another uncounted sub pixel subregion is on the edge before the next vertex; based on determining that no starting point is on the edge before the vertex, adding coordinates of the next vertex to the path and continuing the navigating in the predetermined direction toward the next vertex; and based on determining that there is a starting point to a segment of another uncounted sub pixel subregion on the edge before the vertex, navigating through the pixel along a segment to an intersection between a point of the contiguous points comprising the other uncounted sub pixel subregion and an edge of the pixel, adding the contiguous points to the path, marking the other uncounted sub pixel subregion as counted, and progressing from the intersection in the pre-determined direction to another vertex.

In some examples of the computer program product, the predetermined direction is selected from the group consisting of: clockwise and counterclockwise.

In some examples of the computer program product, utilizing, the one or more sub pixel subregions to determine the combined area of sub pixel subregions comprises: determining, by the one or more processors, an area for each sub pixel subregion; and adding, by the one or more processors, each determined area together to generate the combined area of sub pixel subregions.

In some examples of the computer program product, the method comprises generating, by the one or more processors, a pixel dictionary; and updating, by the one or more processors, the pixel dictionary to include the set of points, wherein a portion of the set of points comprises edge points.

In some examples of the computer program product, the method comprises generating, by the one or more processors, a dictionary identifying edge pixels, wherein the generating comprises, for each pixel in the region of interest: setting, by the one or more processors, an internal area of the pixel to a constant; determining, by the one or more processors, if a center point of the pixel is within the region of interest; based on determining that the center of the pixel is within the region of interest, determining, by the one or more processors, if the center point is an edge point in the pixel dictionary; based on determining that the center point is the edge point, determining, by the one or more processors, if an edge area of the pixel is greater than zero; and updating, by the one or more processors, the pixel dictionary to include the pixel as an edge pixel.

In some examples of the computer program product, the constant is 1.

Systems, methods, and computer program products relating to one or more aspects of the technique are also described and may be claimed herein. Further, services relating to one or more aspects of the technique are also described and may be claimed herein.

Additional features are realized through the techniques described herein. Other examples and aspects are described in detail herein and are considered a part of the claimed aspects. These and other objects, features and advantages of this disclosure will become apparent from the following detailed description of the various aspects of the disclosure taken in conjunction with the accompanying drawings.

It should be appreciated that all combinations of the foregoing aspects and additional concepts discussed in greater detail below (provided such concepts are not mutually inconsistent) are contemplated as being part of the inventive subject matter and to achieve the advantages disclosed herein.

BRIEF DESCRIPTION OF DRAWINGS

One or more aspects of the present invention are particularly pointed out and distinctly claimed as examples in the claims at the conclusion of the specification. The foregoing and objects, features, and advantages of one or more aspects of the invention are apparent from the following detailed description taken in conjunction with the accompanying drawings.

DETAILED DESCRIPTION OF THE INVENTION

Figure 1:
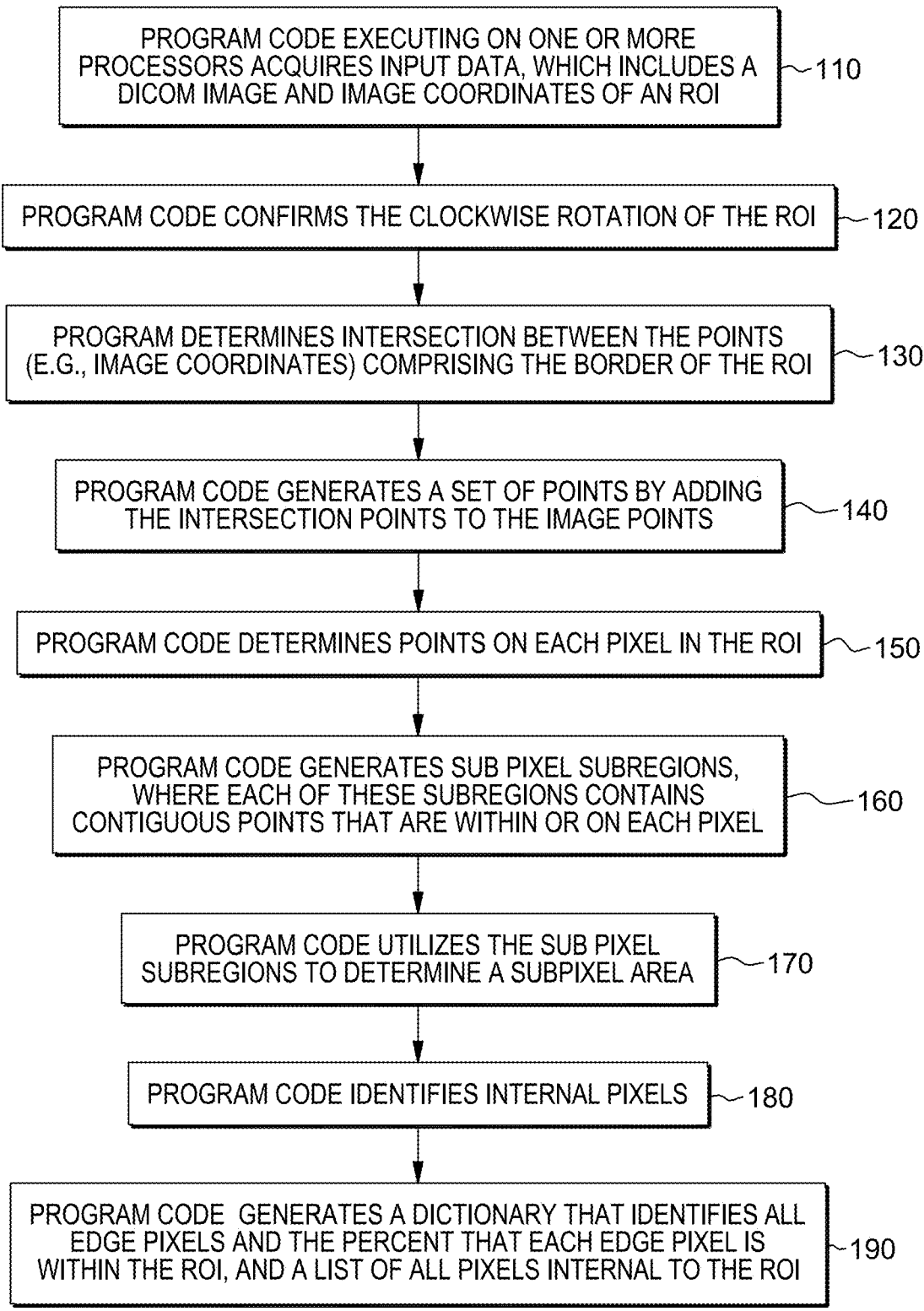
FIG. 1 is a workflow that depicts various aspects of some embodiments of the present invention.

Aspects of the present invention and certain features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the invention in detail. It should be understood, however, that the detailed description and the specific examples, while indicating aspects of the invention, are given by way of illustration only, and not by way of limitation. Various substitutions, modifications, additions, and/or arrangements, within the spirit and/or scope of the underlying inventive concepts will be apparent to those skilled in the art from this disclosure. The terms software and program code are used interchangeably throughout this application and can refer to logic executed by both hardware and software. Components of the system that can be utilized to execute aspects of embodiments of the present invention may include specialized hardware, including but not limited to, an FPGA and a GPU (graphics processor unit). Additionally, items denoted as processors may include hardware and/or software processors or other processing means, including but not limited to a software defined radio and/or custom hardware.

As noted above, as understood by one of skill in the art, program code, as referred to throughout this application, includes both software and hardware. For example, program code in certain embodiments of the present invention includes fixed function hardware, while other embodiments utilized a software-based implementation of the functionality described. Certain embodiments combine both types of program code. One example of program code includes a program/utility, having a set (at least one) of program modules, stored in a memory.

Embodiments of the present invention includes computer systems, computer program products, and computer-implemented methods in which program code executed by one or more processors renders or draws one or more regions of interest (ROIs) on an image, including but not limited to, a DICOM image. As will be discussed in greater detail herein, in some embodiments, the program code generates the regions by superimposing (including via annotations) points at locations identified by the program code on the images and performing calculations described herein based on the identified locations. The program code in embodiments of the present invention utilizes pixels with the rendered ROI to determine a standard uptake value (SUV). As will be discussed in additional detail herein, in embodiments of the present invention, to determine an SUV, the program code performs various aspects, which include, but are not limited to: 1) obtaining input data, including but not limited to a (DICOM) image and coordinates for a rendered ROI; 2) confirming a clockwise rotation of the ROI; 3) determining pixel intersections between points; 4) identifying points of each pixel; 6) generating subpixel regions; and/or 7) determining internal pixels based on the generated regions.

Embodiments of the present invention are inextricably linked to computing at least because they include a unique processing of an image, such as a DICOM image. At least the mapping and interpretation of points on a DICOM image are all aspects that are unique to computing. Also, as will be noted below, the image processing described herein represents an improvement to existing image processing technologies in this arena because the speed of anomaly identification and the accuracy of the anomaly identification is also increased. Additionally, the granularity of the image analysis, manipulation, and generation of additional objects utilizes features and aspects that are inextricable from computer systems.

Embodiments of the present invention, in addition to being inextricably tied to computing, also provide a practical application. For example, the image analysis, rendering, and computations described herein, identify, isolate, calculate, and provide data in an image regarding an SUV. In a non-limited example, a determination, by the program code, of an SUV, can assist a medical professional in making a cancer diagnosis (identifying a malignant abnormality), understand the progression or recession of existing cancer cells, and/or assist the medical professional in providing a course of treatment. In embodiments of the present invention, the program code isolates an ROI using the smallest possible subregions such that areas in interest are more readily and quickly identified. Isolating these subregions is a practical application at least because determining what pixels are to be enclosed in an ROI, as accomplished in embodiments of the present invention by the program code, is useful in understanding precise measurements regarding the absorption of radio-active sugars and the density of the absorption. Each pixel has a given value and embodiments of the present invention determine which pixels to include in the ROI and the weight to be given to each pixel selected for inclusion. The inclusion and/or exclusion of pixels in the subregions takes on specific importance in particular applications, including but not limited to, when utilized in the medical field to where it can be used to observe treatment regimens and plan future treatment regimens. As will be discussed in greater detail herein, aspects of various embodiments of the present invention includes program code executing on one or more processors generating a dictionary that identifies all edge pixels and the percent that each edge pixel is within the ROI, and a list of all pixels internal to the ROI. This data can be utilized to efficiently and accurately isolate data from a DICOM image.

As will be discussed in greater detail herein, various embodiments of the present invention include aspects that represent significant improvements over existing technologies utilized to generate, analyze, and/or further utilize ROIs identified in DICOM images. Specific non-limiting examples are included later in this disclosure to demonstrate the gains in accuracy and efficiency provided by aspects of some embodiments of the present invention. However, generally, benefits provided by aspects of embodiments of the present invention over existing approaches include, but are not limited to: 1) a more accurate representation (based on data provided) of the size of an anomaly in a DICOM image; 2) information about the SUV and the ROI that enable more accurate dosing; and 3) a clearer representation, via both visuals as well as supporting data, of the efficacy of a treatment plan. Put plainly, aspects of various embodiments of the present invention enable an isolation of pixels that reduces extraneous or missing information and appropriately weights edges on an ROI.

Figure 13:
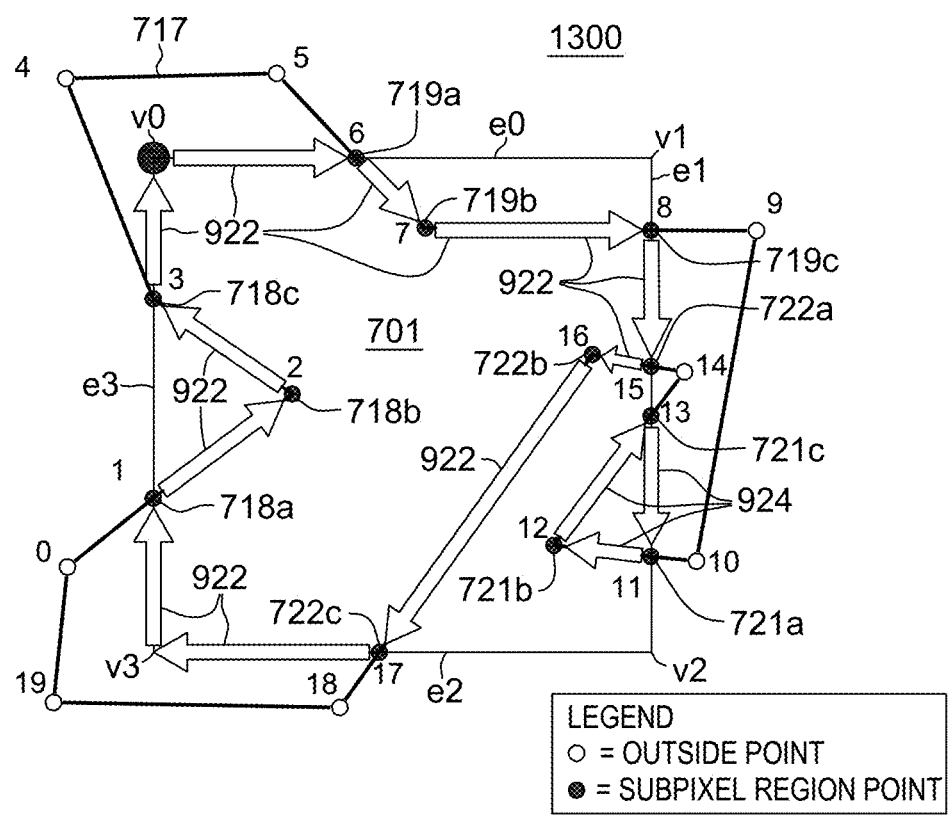
FIG. 13 depicts various aspects of some embodiments of the present invention and includes a portion of progression of the program code throughout a pixel to define subpixel areas within the pixel.
Figure 14:
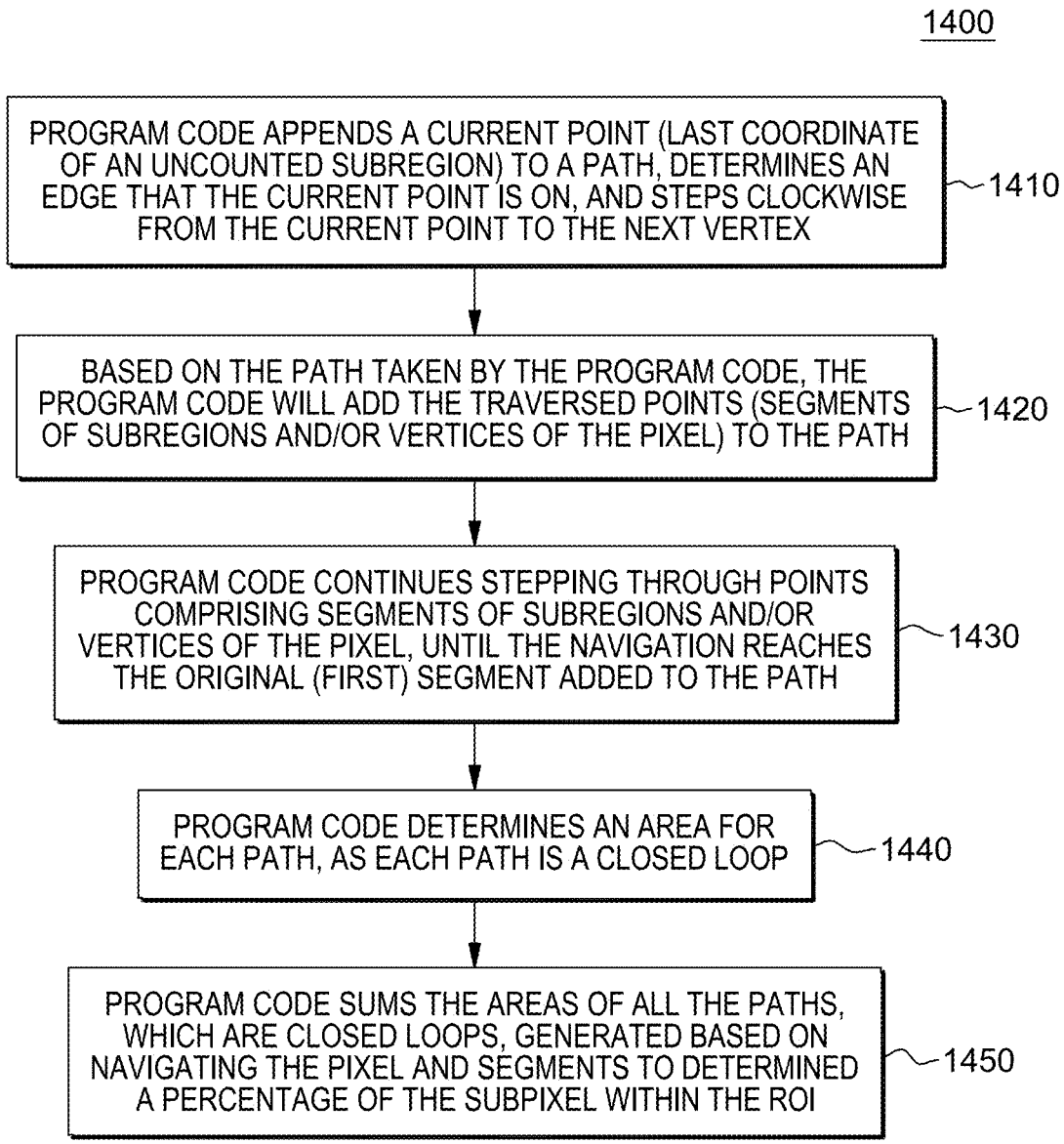
FIG. 14 is a workflow that depicts various aspects of some embodiments of the present invention.
Figure 15:
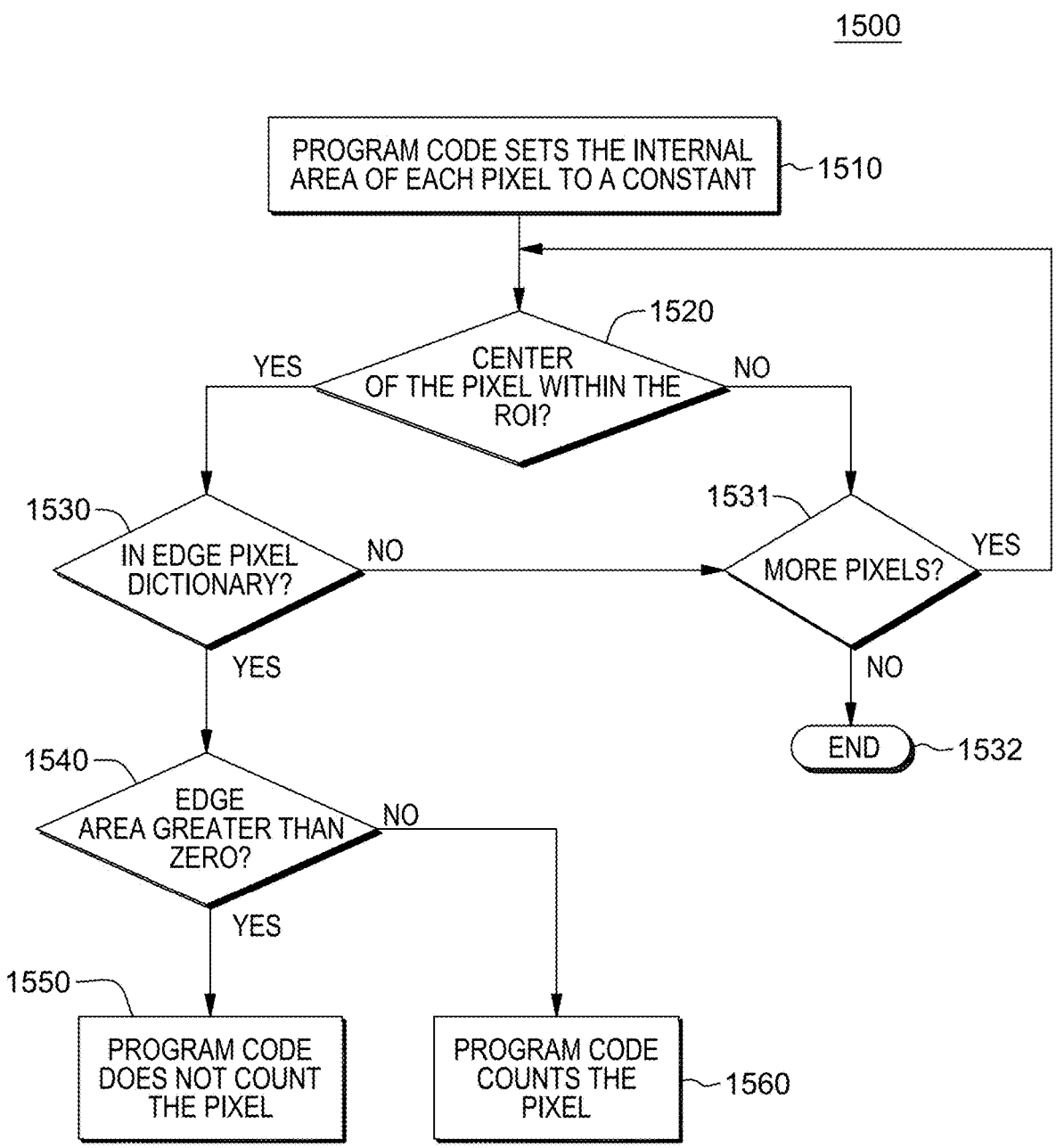
FIG. 15 is a workflow that depicts various aspects of some embodiments of the present invention.

FIG. 1 provides a general workflow 100 of various aspects of some embodiments of the present invention. Throughout the workflow 100 of FIG. 1, additional figures are referenced to illustrate various aspect described more generally in FIG. 1. The workflow 100 of FIG. 1 illustrates how program code in embodiments of the present invention models an ROI, including but limited to utilizing existing imaging and modeling tools, such as, for example, Synapse®. Synapse® is a product of FUJIFILM Medical Systems U.S.A., Inc., and is a registered trademark of FUJIFILM Medical Systems U.S.A., Inc., Lexington, MA (USA). Existing solutions, including but not limited to Synapse®, may include various computer programs utilized for management of patient specific image-related information for use by healthcare providers for reviewing past medical history and radiologic images for the primary diagnosis and care of patients. Certain aspects described herein can be integrated into these various existing solutions or can work in concert with these solutions, becoming enhancements. As understood by one of skill in the art, Synapse® is provided as a non-limiting example, for illustrative purposes only, and not to suggest any limitations. As illustrated throughout the workflow 100 for FIG. 1 and the additional figures, the program code can utilize aspects of some existing tools or not to draw the ROI on a DICOM image. The program code draws this ROI by annotating the image with various points, and performing calculations based on the annotations. The program code then determined the SUV utilizing the pixels (identified by the program code) within the ROI. Thus, the program code determined what pixels are within an ROI and what percentage of each pixel is within the ROI, for any given trace. As noted, FIGS. 2-13 and 16 expand upon the aspects generally described in the workflow 100 (FIG. 1) to provide further illustration. FIGS. 14-15 are workflow 1400, 1500, which provide additional detail on aspects of the workflow 100 of FIG. 1. As understood by one of skill in the art, various examples provided herein are selected so that they can be easily understood and illustrated. However, program code in embodiments of the present invention executes various aspects of the invention on complex DICOM images including those images in which the pixels and subpixels identified and explored herein cannot be recognized by an individual without the assistance of computing technology.

Figure 2:
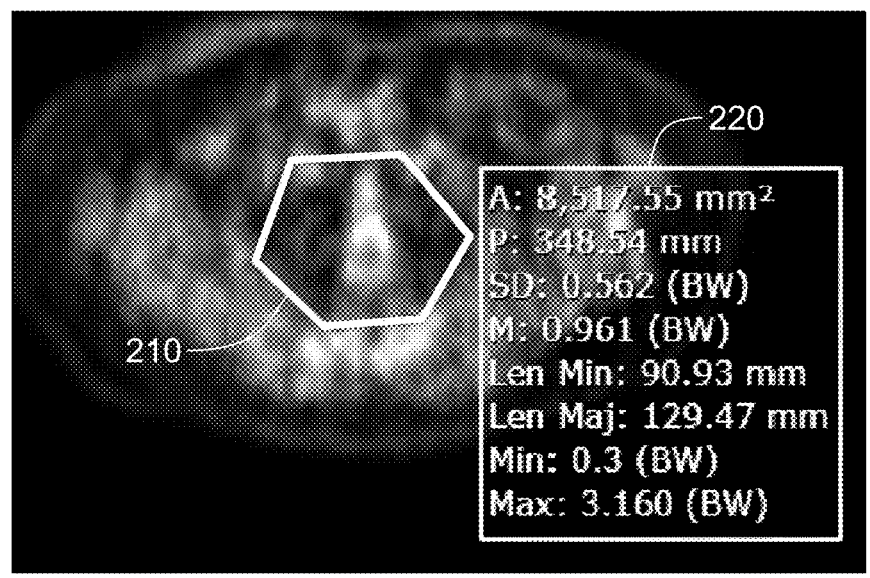
FIG. 2 depicts a DICOM image with data that can be utilized as input data in various embodiments of the present invention.
Figure 3:
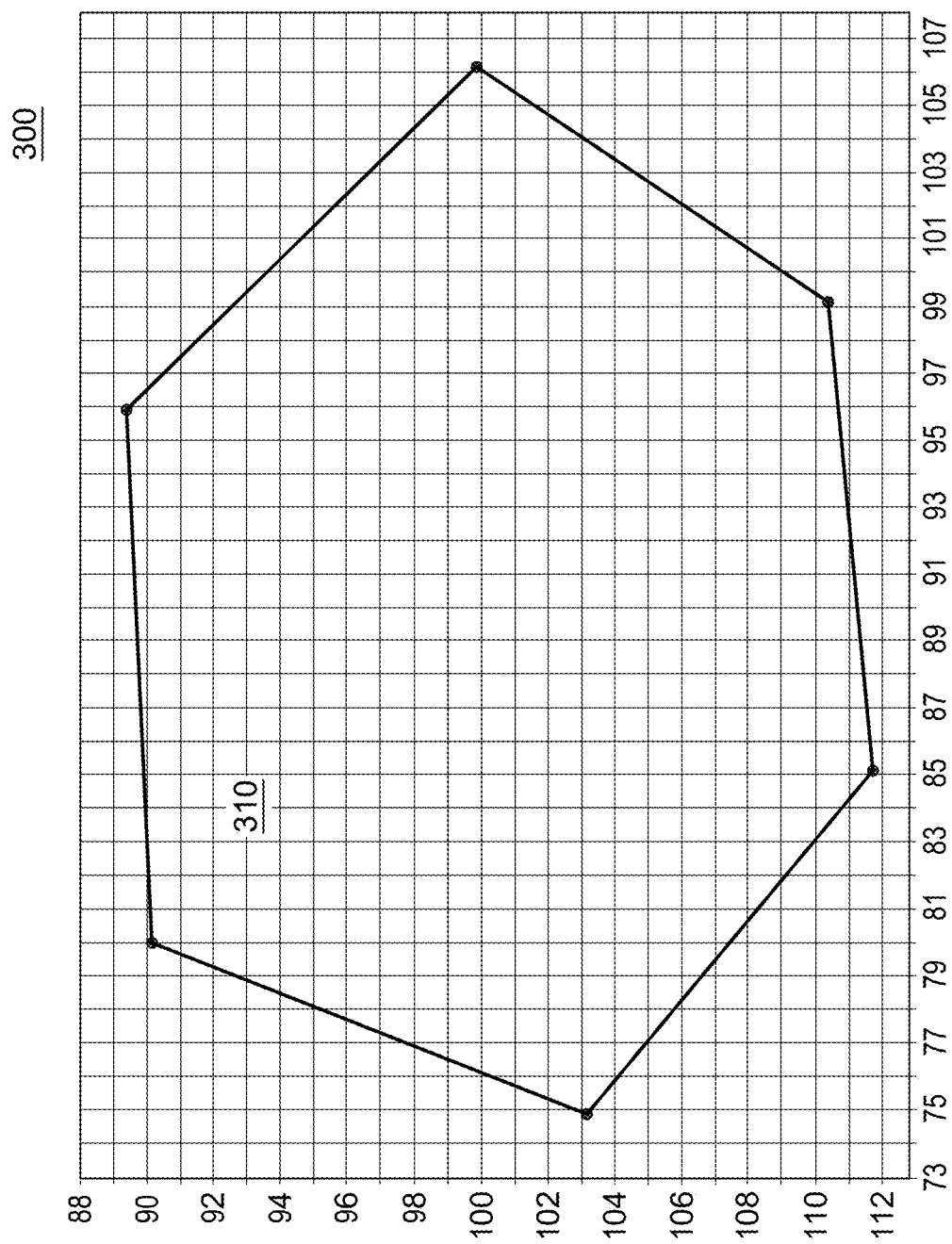
FIG. 3 is an example of a rendering of an ROI by the program code in some embodiments of the present invention.

Referring to FIG. 1, in this workflow 100, in some embodiments of the present invention, program code executing on one or more processors acquires input data, which includes a DICOM image and image coordinates of an ROI (110). FIG. 2 is an example of a DICOM image which can be acquired by the program code in some embodiments of the present invention. Identified in the DICOM image 200, is an ROI 210, which is a closed region of points. Various measurements 220 related to the specific ROI 210 in the image 200 are also provided, for illustrative purposes, but these data are obtained by the program code. The program code also obtains the coordinates defining the ROI, which the program code reproduces on a two-dimensional axis, generating a computer model of the ROI, based on the coordinates (e.g., [[x_0, y_0], [x_1, y_1], [x_2, y_2], . . . ] where x/y are the image coordinates of the image, and [0, 0] is the origin, which is the top left corner of the image; image coordinates can be floats, such as [0.5, 0.5] which is the center of the top left pixel). FIG. 3 is an example of a rendering 300 of the ROI 310 by the program code on an x and y axis. Hence, all the coordinates of the boundaries of the ROI 210 310 are illustrated in FIGS. 2 and 3.

Returning to FIG. 1, the program code confirms the clockwise rotation of the ROI (120), which is defined by the coordinates obtained by the program code. The program code rotates around the points in a clockwise direction. The ordering of the confirmation maintains consistency throughout the methods described herein. For example, in some embodiments of the present invention, the program code determines/locates a point within the ROI. The program code starts at a first point of the determined points and calculates an angle between this point and the next point. If the angle is positive, the rotation is counterclockwise, if negative, clockwise. The program code adds the angle to a total and repeats these calculations for all points. If the total angle of rotation is negative, the points rotate clockwise. If the total angle is positive (counterclockwise rotation), the program code reverses the order of the points so that the rotation is clockwise. In this manner, the program code walks clockwise to identify pixels of which certain parts are in the ROI and which pixels so not include any regions that are within the ROI. By walking through the pixels in a consistent manner, e.g., clockwise, the program code can track which pixels have been included, based on a first location in each pixel. As understood by one of skill in the art, it is the consistency of this path that enables the program code to navigate points of a perimeter in this aspect. Thus, a counterclockwise or other directional navigation could be employed in other embodiments provided that the program code maintains consistency during its navigation from a first point to a second point and moving forward around the perimeter.

Figure 4:
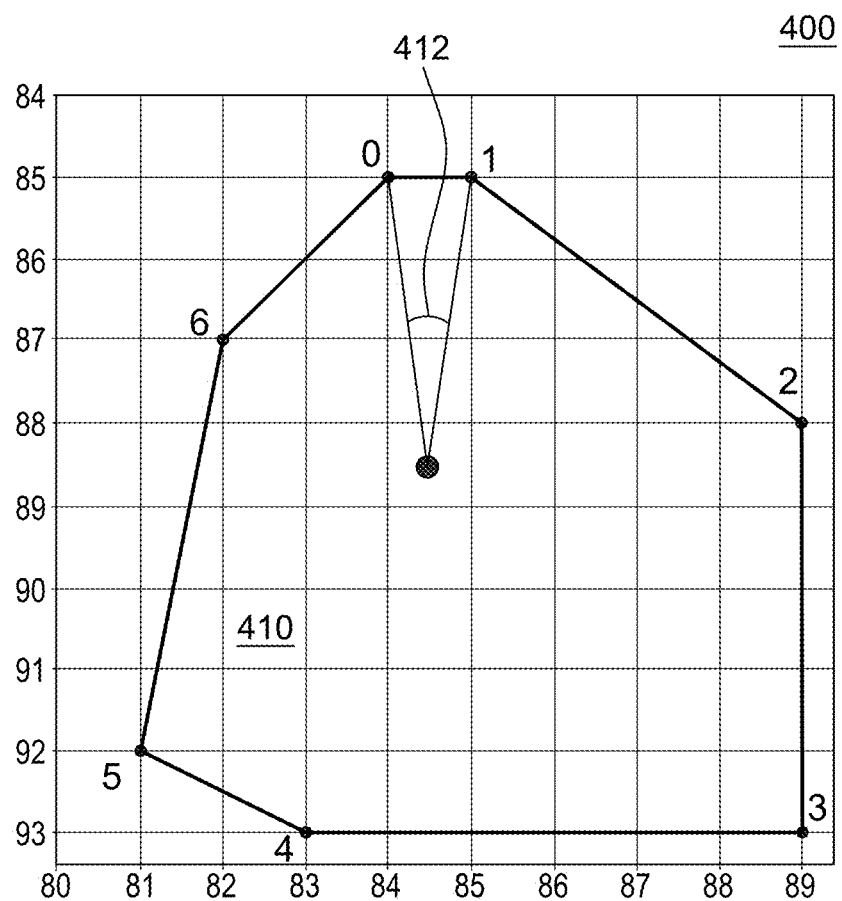
FIG. 4 illustrates the navigation or walk of the program code in various embodiments of the present invention from a first point to a second point around a two-dimensional representation of an ROI.

FIG. 4 illustrates the navigation or walk 400 of the program code from a first point to a second point around the two-dimensional representation of the ROI 410 defined by the program code, based on obtaining coordinates from an image (e.g., FIG. 2, 200). FIG. 4 provides a non-limiting example of an ROI shape that is navigated by the program code. The shape on the ROI 410 displayed in FIG. 4 was selected for illustrative purposes only and not to suggest any limitations. Referring to FIG. 4, points 0, 1, 2, 3, 4, and 5 represent points on a boundary on an ROI 410. The program code identifies an angle of rotation 412 between a first point, 0, and a second point, 1. The angle 412 between the first point, 0, and the second point, 1, is negative and hence, the program code determines that the rotation is clockwise. The program code continues this navigation from each point to the next and determine the angle between each of these points. The program code calculates a sum of the angle and provided the total is negative, the navigation has been clockwise. In this example, the navigation around the ROI is started at point 0, however, in embodiments of the present invention, a navigation can be started at any point provided that the order (clockwise) is maintained to avoid duplication or omission in the navigation; duplication and omission would adversely affect the results. As aforementioned, an advantage of aspects of various examples herein is that the information provided in the result, the pixel sub-region, is more complete, comprehensive, and efficient that information provided by existing image region isolation technologies.

Figure 5:
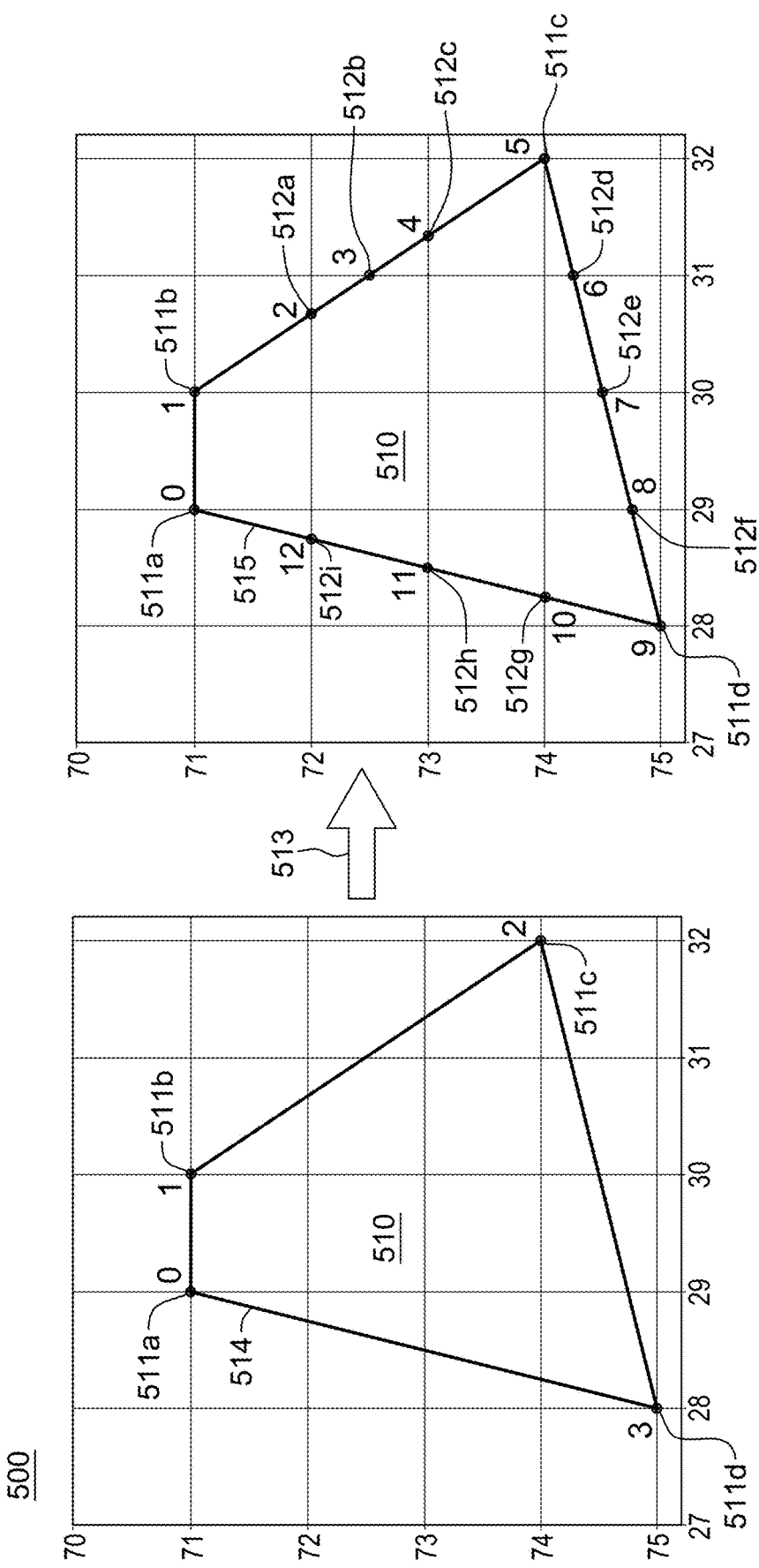
FIG. 5 illustrates how the program code in various embodiments of the present invention utilizes an ROI defined by connections between image points to generate an updated model.

Referring to FIG. 1, in some embodiments of the present invention, the program determines intersection between the points (e.g., image coordinates) comprising the border of the ROI (130). In this context, a pixel intersection is any time the ROI intersects with an edge of the pixel. FIG. 5 illustrates a progression 500, specifically, how the program code utilizes an ROI 510 defined by connections between image points 511*a*-511*d*, and updates (513) this model 514 to generate an updated model 515 of the same ROI 510, now framed by both the image points 511*a*-511*d* and the intersections points generated by the program code 512*a*-512*i*. The shape of the ROI in FIG. 4 differs from that in FIG. 5 just to provide further illustrations that demonstrate the functionality of various examples disclosed herein regardless of the shape of the ROI. The sequence of the points, both image points and intersection points, around the ROI is maintained for illustrative purposes only, but the differences in the types of points is differentiated in certain of the labelling. The intersection points 512*a*-512*i* are pixel intersections between adjacent image coordinates calculated by the program code. As illustrated in FIGS. 1 and 5, the program code generates a set of points by adding the intersection points to the image points (140). An example of a set of points comprised on image and intersection points are the points labeled 0-12 in the updated model 515.

Returning to FIG. 1, in this example, the program code determines points on each pixel in the ROI (150). To make this determination, the program code generates a dictionary of pixels by looping through each point in the set of points and points that are within or on the edge of each pixel. The examples herein utilize a numbering scheme in order to maintain consistency throughout the aspects described. As understood by the art, a different scheme can be utilized provided that the consistency can be maintained. Hence, in this example, the pixels which are looped through by the program code are numbered such that: pixel [0, 0] ([x, y]) is pixel 0; pixel [1, 0] is pixel 1; pixel [n, 0] is pixel_n−1; pixel [0, 1] is pixel_n. Hence, the pixel and point dictionary format of the dictionary generated by the program code is {pixel_n: [([x, y], i), . . . ], . . . } where { }=dict, where [ ]=array, ( )=tuple, where pixel_n=the pixel number, where [x, y]=position of the point in image coordinates, and where i=the number of the point. In the examples herein, the first point has number 0, the second number 1, etc.

Figure 6:
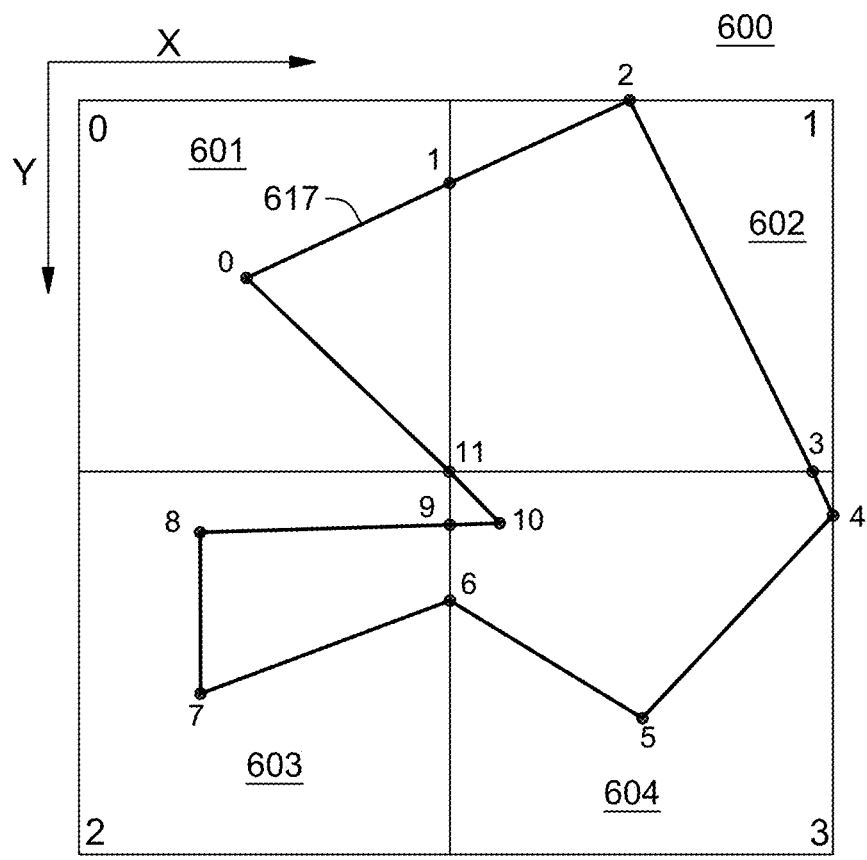
FIG. 6 illustrates the program code in various embodiments of the present invention determining points on each pixel in an ROI.

FIG. 6 illustrates the program code determining points on each pixel in the ROI (e.g., FIG. 1, 150). The x and y axis are labeled in FIG. 6, as are four pixels 601-604, which are labeled 0-3. Both numberings are retained to accommodate the dictionary format discussed above. The points comprising the dictionary of pixels, which the program code generated by looping through each point in the set of points and points that are within or on the edge of each pixel, are all found along a path 617 and are labeled 0-11. The numbers along the path 617 can be understood as a combined points number. A position of each point on the x and y axis is expressed herein in a [x, y] format. Hence, in this example, the points in a first pixel 601 (also labeled 0), determined by the program code, are 0, 1, and 11 (along the path 617). The points in a second pixel 602 (also labeled 1), are 1, 2, 3, and 11. In a dictionary generated by the program code, the points generated in each, including pixel number, location, and point number, can be formatted as follows: {pixel number: [([x coordinate, y coordinate), point number along path], ([x coordinate, y coordinate], next point number along path), etc.]}. Thus, the dictionary entry (for points along the path 617) generated by the program code for the first pixel 601 in this example is {0: [([0.5, 0.5], 0), ([1, 0.25], 1), ([1, 1], 11)]}. The dictionary entry (for points along the path 617) generated by the program code for the second pixel 602 in this example is {1: [([1, 0.25], 1), ([1.4, 0], 2), ([1.9, 1], 3), ([1, 1], 11)]}.

Returning to FIG. 1, based on determining the points on the pixels, the program code generates sub pixel subregions, where each of these subregions contains contiguous points that are within or on each pixel (160). To generate the subregions, the program code loops or navigates through all points within the given pixel. While navigating, the program code determined if the difference in "i" between the next point and the current point is 1. If the difference is 1, the program code adds this point to the subregion, if not, the program code creates a new subregion. A subregion contains contiguous points that are within or on the pixel and a format that can be utilized is: {"Points": [[x, y], . . . ], "Counted"=False}. The "Counted" designator is a flag that is set to False by default. Once the program code counts the points for a subpixel area, the program code sets the flag to True. The use of this flag maintains consistency throughout this aspect. However, as understood by one of skill in the art, a different value (e.g., data, metadata, a registry entry) can be utilized to track whether a given point is assigned to a subpixel area. As noted above, the program code maps (e.g., acquires) a given subpixel region by: 1) navigating or looping through all points within the given pixel; and 2) if the difference in "i" between the next point and the current point is 1, adding this point to the subregion and if not, create a new subregion.

Figure 7:
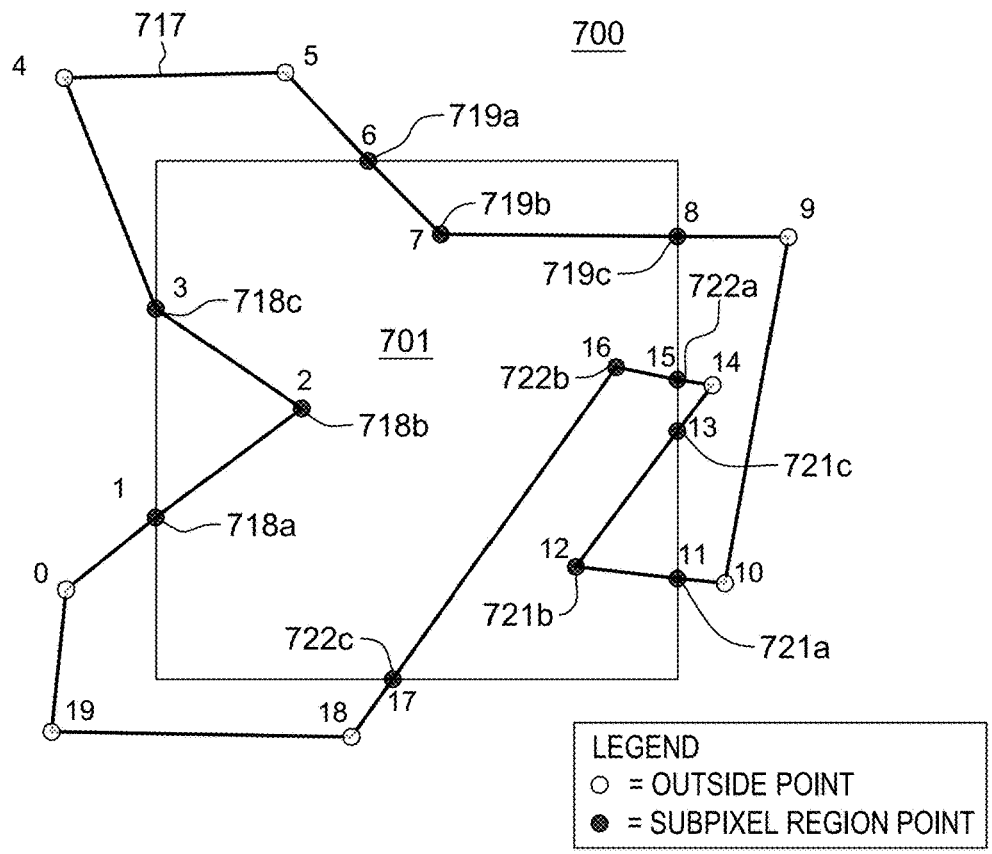
FIG. 7 illustrates a pixel upon which the program code in various embodiments of the present invention has made determinations regarding various points.

FIG. 7 illustrates a pixel 701 upon which the program code has determined the points (e.g., FIG. 1, 150). The example 700 illustrated in FIG. 7 includes both a pixel 701 and a path, as determined by the program code, the pixel 701 and a path 717 of points, where some of the points are inside or intersect an edge of the pixel 701 (e.g., points 1, 2, 3, 6, 7, 8, 11, 12, 13, 15, 16, and 17), and some of the points are outside of the pixel 701 (e.g., points 0, 4, 5, 9, 10, 18, and 19). Based on navigating or looping through all points within the given pixel and evaluating whether the differences between sequential points is 1, the program code, in this example, has generated four different subregions. A first subregion includes points labeled 718a-718c (also labeled 1, 2, and 3). A second subregion includes points labeled 719a-719c (also labeled 6, 7, and 8). A third subregion includes points labeled 721a-721c (also labeled 11, 12, and 13). A fourth subregion includes points labeled 722a-722c (also labeled 15, 16, and 17).

Figure 8:
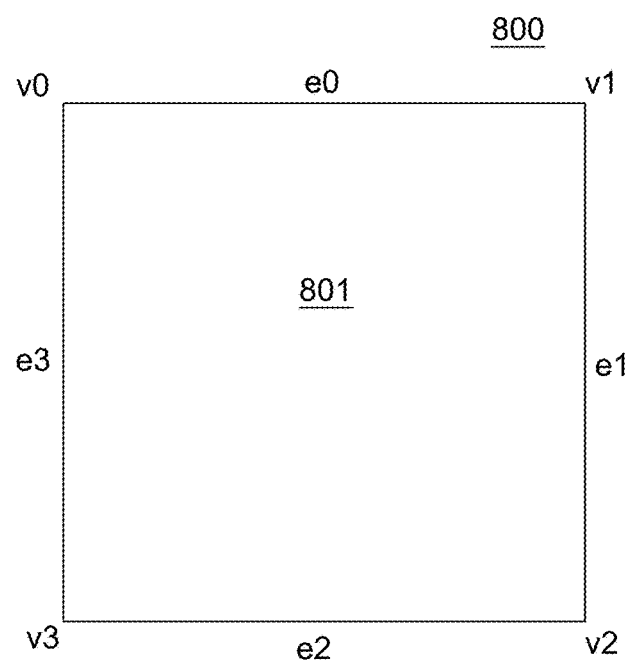
FIG. 8 is a model that is utilized by the program code in various embodiments of the present invention in determining subpixel area.

Referring to FIG. 1, once the program code has created the sub pixel subregions (160), the program code utilizes the sub pixel subregions to determine a subpixel area (170). FIG. 8 is a model 800 that is utilized by the program code in determining a subpixel area (e.g., FIG. 1, 170). Various aspects illustrating the program code determining the subpixel area (e.g., FIG. 1, 170), are further illustrated in FIGS. 9-13. Specifically, FIG. 8 provides an example of a pixel 801 around which the program code navigates (together with points in a subregion which intersect the edges of the pixel 801), to generate a closed loop inside of the pixel 801 that includes points in the pixel 801 as well as vertices of the pixel 801. Referring to FIG. 8, in this exemplary (and non-limiting) model 800, in the pixel 801, the top left, top right, bottom right, and bottom left of a pixel 801 are vertices v0, v1, v2, and v3, respectively and the top, right, bottom, and left edges of the pixel 801 are edge0, edge1, edge2, and edge3 (also referred to as e0, e1, e2, and e3), respectively. As will be illustrated in FIGS. 9-13, the program code counts each subregion it generated, based on navigating a consistent path around the pixel (e.g., FIG. 8, 801). As will be further illustrated in FIG. 9-13, the program code will continue to navigate around the pixel 801 until all the subregions are counted and the points that comprise the subregions are added to a path maintained by the program code. In some embodiments of the present invention, the program code generates an array to store the points comprising each path. Because certain of the aspects generated by the program code are included in FIGS. 9-13, which were previously illustrated in FIGS. 7-8, certain of the labels for aspects in FIGS. 7-8 are reused in FIGS. 9-13. Meanwhile, FIG. 14 is a workflow 1400 that includes various aspects of the examples illustrated in FIGS. 8-13. Thus, as FIGS. 8-13 are discussed in further detail below, reference is made to aspects of the workflow 1400 of FIG. 14.

As will be illustrated in FIGS. 9-13, for each pixel (e.g., FIG. 8, 801), the program code loops through all sub pixel subregions (generated by the program code). The program code generates a dictionary of an area generated from the looping with various values, including but not limited to: 1) {pixel_n: area}; 2) pixel_n=number of the pixel; and 3) area=percent that the pixel is within the ROI. As will be illustrated in certain of the figures that follow, the program code generates a closed loop inside of the pixel 701, 801 composed of the combined points and pixel vertices. In order to generate this loop, the program code creates a new array to hold a current path of the program code.

Figure 9:
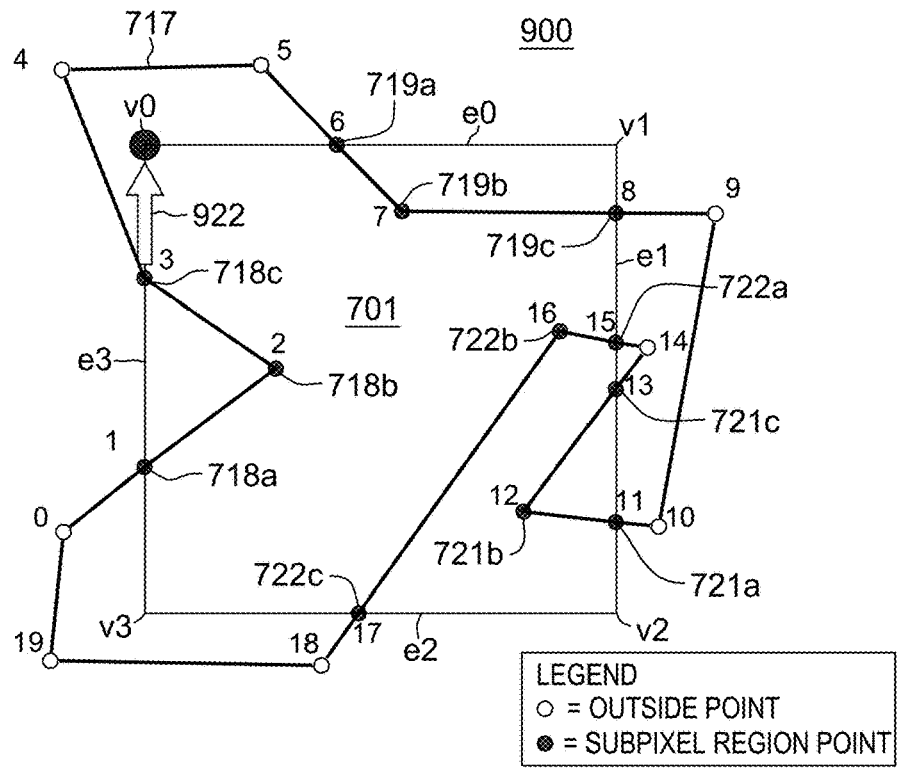
FIG. 9 depicts various aspects of some embodiments of the present invention and includes a portion of progression of the program code throughout a pixel to define subpixel areas within the pixel.

Referring to FIG. 9, as aforementioned, the points of the ROI (and hence all contiguous points within the ROI) rotate clockwise. Thus, the program code starts at a given point and generates a clockwise path 922 around the pixel 701. As depicted in FIG. 14, beginning with the last coordinate (a current point) of an uncounted subregion, the program code appends this point to the (current) path, determines an edge of the pixel 701 where the current point is located (e.g., if the point is on the top of the pixel, it is on edge 0 (see, e.g., FIG. 8)) and from this current point, the program code begins step/navigate clockwise toward a next vertex (1410). Based on the path taken by the program code, the program code will add the traversed points and vertices to the path (1420). For example, referring to FIGS. 8-13, if the point is on edge 0, the next vertex is v1, if the point is on edge 3, the next vertex is v0, and if there is a starting point to another segment between the current point and the target vertex (i.e., the closest vertex to the starting point when moving clockwise from the starting point), the program code will add the points of the subregion to the path, navigating from the earlier current point to a new current point that is the last point of that subregion. Thus, the program code adds points traversed during this navigation to the path, which can include, depending on the configuration of the subregions within the pixel, one or more of the vertices and/or, the points of a subregion. Once the program code navigates a subregion, the subregion is counted by the program code. In this navigation, if there are multiple starting points to different subregions, the program code adds the points of the subregion whose starting point is closest to the current point. If there is no starting point to another segment, the program code adds the vertex to the path, designating this vertex a new current point.

FIGS. 9-13 depict a non-limiting example of the program code navigating subpixel regions within a pixel (e.g., FIG. 14, 1410, 1420). Referring, to FIG. 9, the program code starts at a point at the end of the first subregion (i.e., 3), which includes 718a-718c, and searches for the beginning of the first subregion (e.g., FIG. 14, 1410). The program code walks from e3, the third edge of the pixel according to the model 800 in FIG. 8, from point 3 (718c) to the vertex v0. The program code determines that there is no segment of a subregion that starts on this path 922 and thus, v0 is added to the path 922 (the path 922, as depicted in FIG. 9 is between point 3 (718c) and v0). In FIG. 9, there are four subregions (a first subregion 718a-718c (points 1, 2, and 3), a second subregion 719a-719c (points 6, 7, and 8), a third subregion 721a-721c (points 11, 12, and 13), and a fourth subregion 722a-722c (points 15, 16, and 17). Between point 3 v0 on e3, there is no starting segment of a subregion. As noted above, if there is no starting point to another segment, the program code adds the vertex to the path, designating this vertex a new current point. Thus, as the program code continues its navigation of pixel 701 (which is modeled from pixel model 800, FIG. 8), the vertex v0 becomes the starting or current point. The path 922 can be understood as [point 3, v0] and/or, path=[3, v0] (e.g., FIG. 14, 1420).

Figure 10:
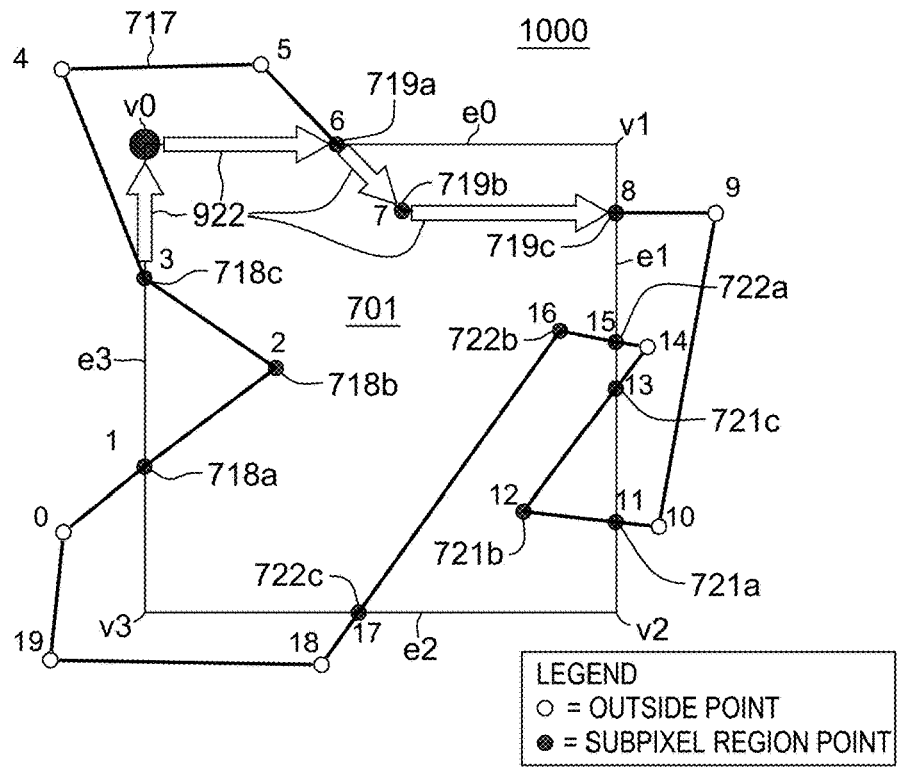
FIG. 10 depicts various aspects of some embodiments of the present invention and includes a portion of progression of the program code throughout a pixel to define subpixel areas within the pixel.

Referring to FIG. 10, the progression of the path 922 by the program code is further illustrated herein. The program code starts at v0 (a new current point, per FIG. 14), picking up from the path 922 of FIG. 9. The program code determines that the second subregion 719a-719c (points 6, 7, and 8), between the starting point, vertices v0, and the ending point, vertices v1, on the edge, e0. Because there is a segment start point, instead of continuing along a path to vertices v1, the program code continues the path 922 along the second subregion 719a-719c (points 6, 7, and 8), to the end of this subregion. The program code adds the points traversed (i.e., points 6, 7, and 8) to the path 922 (e.g., FIG. 14, 1420). Because the second subregion was traversed by the program code in its entirety, it has been accounted for and can be utilized to determine a subpixel area (e.g., FIG. 1, 170). Point 8 (719c) becomes a starting point for the program code to utilize in continuing the path 922. Point 8 (719c) is on the edge e1. As of the navigation illustrated in FIG. 10, the path is comprised of points 3, v0, 6, 7, and 8. Hence, path=[3, v0, 6, 7, 8]. As discussed earlier, as each point in the path can be described in terms of x and y coordinates, the path 922 can also be understood as [[x_3, y_3], [x_v0, y_v0], [x_6, y_6], [x_7, y_7], [x_8, y_8]] where x_i/y_i are the x/y coordinates of point i.

Figure 11:
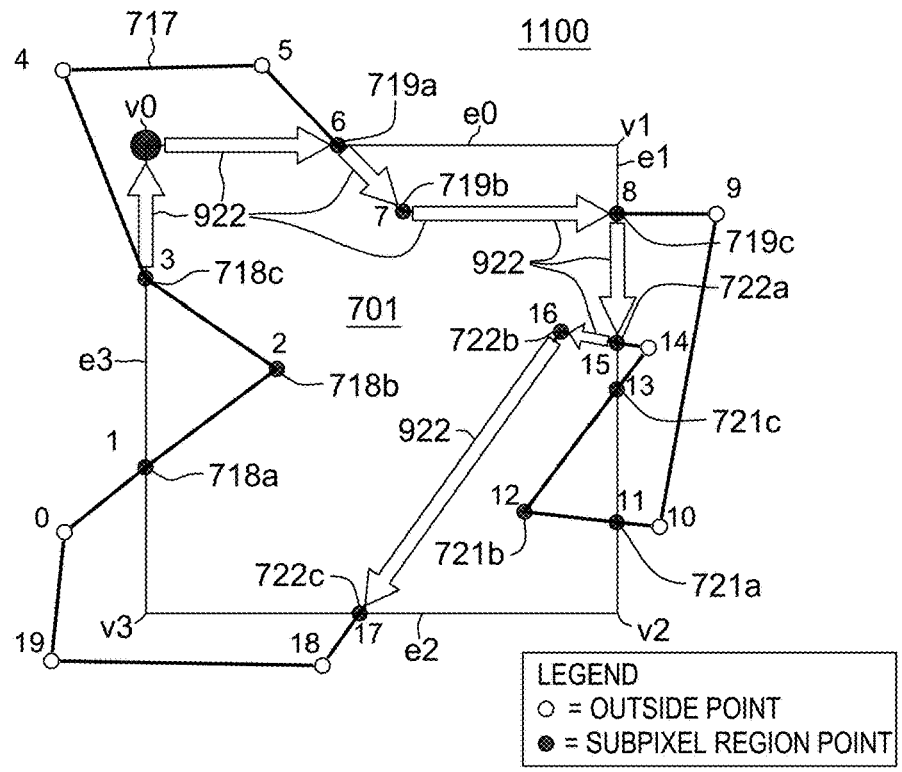
FIG. 11 depicts various aspects of some embodiments of the present invention and includes a portion of progression of the program code throughout a pixel to define subpixel areas within the pixel.
Figure 12:
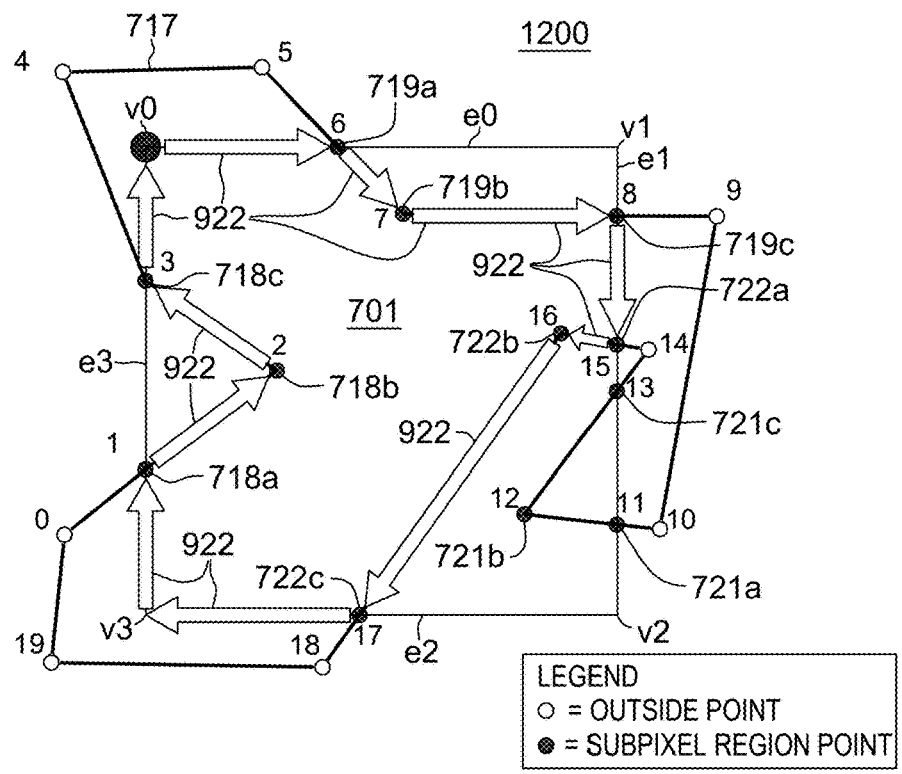
FIG. 12 depicts various aspects of some embodiments of the present invention and includes a portion of progression of the program code throughout a pixel to define subpixel areas within the pixel.

FIG. 11 is a continuation of the example 1100 and illustrates the continuation, by the program code, of the path 922. The program code begins at point 8, as it last navigated there in FIG. 10. The program code moves along the edge e1 to the vertex v2. There are two segment start points that intersect the edge e1, as the program code navigates this edge to the vertex v2. As noted, above, in this example, if there are multiple starting points to different subregions, the program code adds the points of the subregion whose starting point is closest to the current point. In FIG. 11, point 15 is closer to point 8 of the fourth subregion 722a-722c than point 15 is to point 11 of the third subregion 721a-721c. Thus, the program code continues the path 922 along the fourth subregion 722a-722c, adding points 15, 16, and 17 to the path 922 (e.g., FIG. 14, 1420). Because the fourth subregion was traversed by the program code in its entirety, it has been accounted for and can be utilized to determine a subpixel area (e.g., FIG. 1, 170). Point 17 becomes a new starting point. The path, is saved by the program code, is expanded to contain 3, v0, 6, 7, 8, 15, 16, and 17, hence path=[3, v0, 6, 7, 8, 15, 16, 17].

Returning to FIG. 14, the program code continues stepping through points comprising segments of subregions and/or vertices of the pixel, until the navigation reaches the original (first) segment added to the path (1430). Referring to FIG. 13, the program code, continuing its clockwise navigation, navigates from point 17 to vertex v3 based on no segment starting point being present between point 17 and the target vertex (e.g., v3). The program code, en route from vertex v3 to vertex v0, on edge 3 (e3), reaches a starting segment of the first subregion, which includes points labeled 718a-718c (also labeled 1, 2, and 3). Point 3 was the original starting point and has already been added to the path 922. The program code adds the remainder of the first segment to the path 922. Thus, path 922 includes 3, v0, 6, 7, 8, 15, 16, 17, v3, 1, and 2 (path=[3, v0, 6, 7, 8, 15, 16, 17, v3, 1, 2]). Having completed path 922 around the pixel 701, three out of the four subregions have been counted by the program code, with their points added to the path 922. However, the third subregion 721a-721c (points 11, 12, and 13) was not added during the initial navigation of the edges of the pixel 701 and is not part of path 922. The third subregion remains an uncounted subregion. Thus, beginning with the last coordinate of this uncounted subregion, the program code appends this point to the current path, determines the edge where the current point is located (e.g., if the point is on the top of the pixel, it is on edge 0 (see, e.g., FIG. 8)) and from this current point, the program code will attempt to step clockwise to the next vertex (1410). Based on the path taken by the program code, the program code will add certain points to a path (1420). The program code continues stepping through points comprising segments of subregions and/or vertices of the pixel, until the navigation reaches the original (first) segment added to the path (1430). When there are no remaining uncounted subregions, the program code determines an area for each path, as each path is a closed loop (1440). For each area, the program code may or may not check that the area is less than 1, 1 being the internal area of each pixel. The program code then sums the areas of all the paths, which are closed loops, generated based on navigating the pixel and segments (1450). The percentage of the subpixel within the ROI is the combined areas of the paths.

FIG. 13 illustrates how, in this example, upon completing a first path 922, the third subregion 721a-721c (points 11, 12, and 13) was an uncounted subregion. The third subregion was not counted or included in the first path 922 because if there are multiple starting points to different subregions along an edge that the program code is navigating, the program code adds the points of the subregion whose starting point is closest to the current point to the path. When traversing the first path, the program code added the fourth subregion because point 15 of the fourth subregion 722a-722c was closer to the current point, point 8, than point 13 of the third subregion 721a-721c. Thus, having completed the first path 922, the program code, beginning with the last coordinate of the uncounted subregion, point 15 of the third subregion 721a-721c (points 11, 12, and 13), the program code appends this point to the current path, determines the edge that the current point is (e.g., if the point is on the top of the pixel, it is on edge 0 (see, e.g., FIG. 8)) and from this current point, the program code will attempt to step clockwise to the next vertex (1410), adds certain (traversed) points to a path (1420), and continues stepping through points comprising segments of subregions and/or vertices of the pixel, until the navigation reaches the original (first) segment added to the path (1430).

In this non-limiting example, the program code has completed stepping through the subregions after adding the points of the third subregion 721a-721c (points 11, 12, and 13), to the second path 924. In this example, the first path 922 includes the points 3, v0, 6, 7, 8, 15, 16, 17, v3, 1, and 2 (path_1=[3, v0, 6, 7, 8, 15, 16, 17, v3, 1, 2]), and the second path 924 includes the points 13, 11, and 12 (path 2=13, 11, 12). Each path represents a closed loop that forms the bounds of an area within the pixel 701. To determine the subpixel area (FIG. 1, 170), the program code calculates the areas of the paths 922, 924, which are closed loops (e.g., FIG. 14, 1440) and then sums these areas (e.g., FIG. 14, 1450). The combined area of all the subpixel areas for a given pixel are the percentage of the pixel 701 that is within the ROI (when the pixel area is set to a value of 1, making the combined areas, which are less than 1, a percentage of this whole). In some embodiments of the present invention, when the program adds each area to the combined area, the program code checks that each area is less than 1.

Returning to FIG. 1, after the program code determines the subpixel area (170), the program code identifies internal pixels (pixels internal to the subpixel area) (180). The program code generates a list of internal pixels. A format for this list can include, but is not limited to [pixel_n, pixel_n, etc.]. FIG. 15 depicts a workflow 1500 illustrating aspects of the program code determining the subpixel area. In some embodiments of the present invention, the program code sets the internal area of each pixel to a constant, for example, 1 (1510). The program code determines, for each pixel, if the center of the pixel is within the ROI (1520). In order to make this determination, the program code can utilize a proprietary and/or existing method. In some examples, the program code applies a standard algorithm to check if a point is within an ROI by casting a ray out from the point. If the program code determines that the point is within the ROI, the program code determines if it is within the edge pixel dictionary (1530). If not, the program code moves to the next pixel (1531), terminating when there are no more pixels to evaluate (1532). If the pixel is within the edge pixel dictionary, the program code determines if the edge area is greater than zero (1540). If the edge area is greater than zero, the program code does not count the pixel (1550), if the edge area is zero, the program code counts the pixel (1560).

Figure 16:
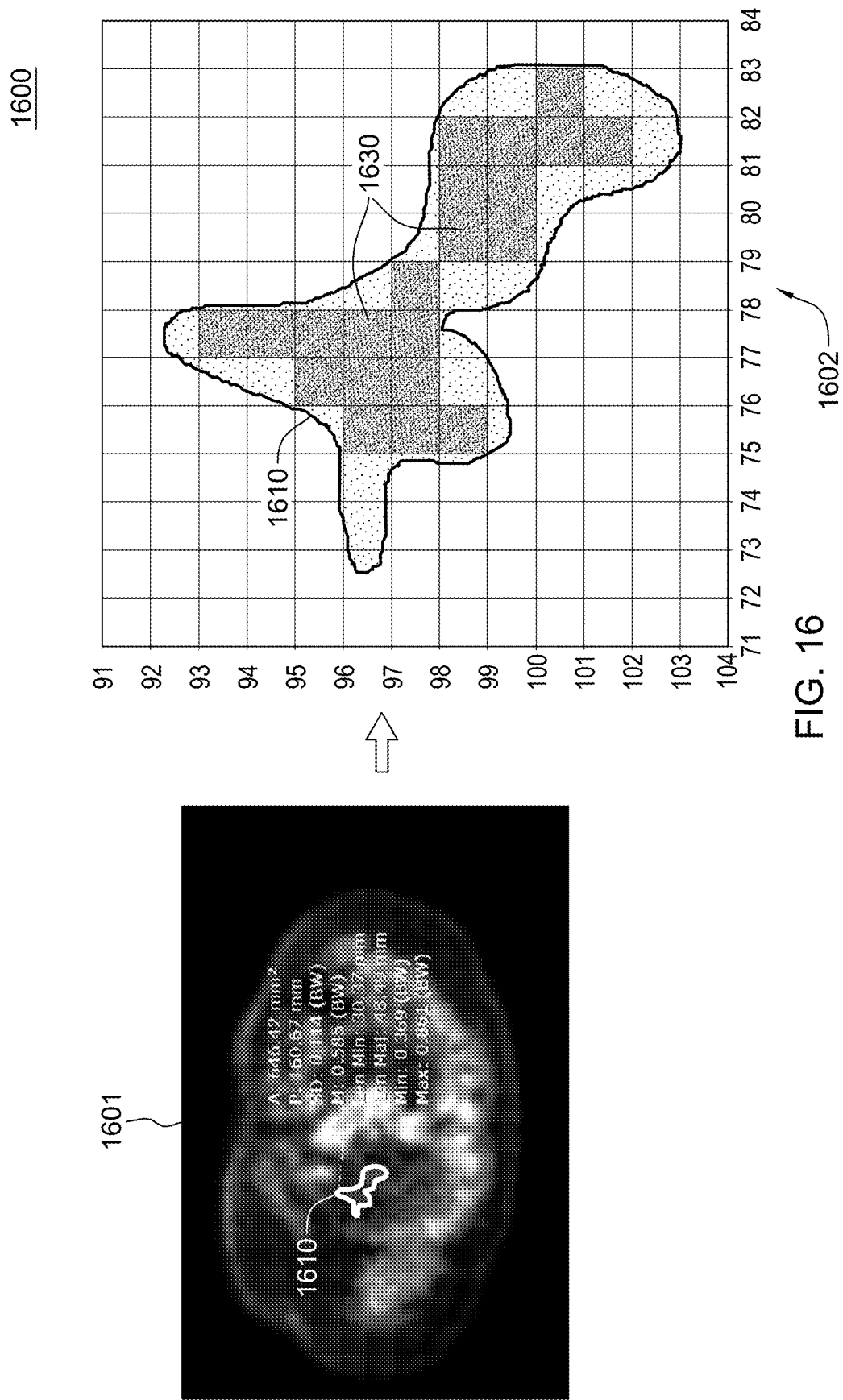
FIG. 16 is an illustration of certain aspects of some embodiments of the present invention.

Thus, returning to FIG. 1, the program code executing on one or more processors generates a dictionary that identifies all edge pixels and the percent that each edge pixel is within the ROI, and a list of all pixels internal to the ROI (190). Thus, the program code can determine an SUV utilizing the pixels within the ROI and what percentage of a pixel is within the ROI for any given trace, which are values that are provided by aspects of embodiments of the present invention. By way of further illustration, FIG. 16 provides an example 1600 of how ROIs 1610 can be drawn on a DICOM image 1601. These regions are created through points placed over the image, and calculations are performed based on the annotation. The aspects of the examples described herein enable the program code to determine a SUV utilizing the pixels 1630 within the ROI, including what percentage of a pixel is within the ROI for any given trace.

Examples of the present invention include methods, systems, and computer program products where program code executing on one or more processors identifies pixels in a region of interest, including what percentage of each pixel is in the region. In some examples, the program code obtains input data comprising an image and image data comprising coordinates defining a region of interest in the image, where each coordinate defines a point on the image, where the image comprises pixels. The program code determines a sequential order for navigating the coordinates defining the region of interest, where the sequential order is non-duplicative of any coordinate of the coordinates. The program code defines a set of points comprising a border around the region of interest, where the defining comprises supplementing the coordinates comprising points in the image by adding additional points comprising intersection points, where each intersection point is an intersection of a line between two coordinates of the coordinates with an edge of a pixel of pixels in the image, where the coordinates comprising points and the intersection points comprise the set of points. The program code determines a combined area of sub pixel subregions in each pixel comprising one or more points in the set of points, the determining comprising: identifying one or more points of the set of points on the pixel; generating based on the one or more points, one or more sub pixel subregions, where each sub pixel subregion comprises contiguous points of the set of points, where the contiguous points are within or on the pixel; and utilizing the one or more sub pixel subregions to determine the combined area of sub pixel subregions.

In some examples, the program code, based on the determining the combined area of sub pixel subregions in each pixel, identifies pixels internal the sub pixel subregions.

In some examples, the program code generates, based on determining the combined area of sub pixel subregions in each pixel and the one or more sub pixel subregions of each pixel, a dictionary identifying edge pixels and a percent of each edge pixel of the edge pixels within the region of interest.

In some examples, the program code generates, based on determining the combined area of sub pixel subregions in each pixel and the one or more sub pixel subregions of each pixel, a dictionary comprising a list of the pixels internal to the regions, where the pixels internal to the regions are internal to the regions of interest.

In some examples, the image is a Digital Imaging and Communications in Medicine (DICOM) image.

In some examples, the sequential order is selected from the group consisting of: clockwise and counterclockwise.

In some examples, utilizing the one or more sub pixel subregions to determine the combined area of sub pixel subregions for each pixel comprises: the program code generating one or more paths, based on navigating along each edge of the pixel, starting with the edge where a current point is located, in a pre-determined direction, toward a next vertex of the pixel, until each sub pixel subregion is counted, the navigating comprises: determining if any of the sub pixel subregions are uncounted; based on determining that at least one sub pixel subregion is uncounted, generating a path comprising contiguous points comprising the at least one sub pixel subregion, the generating comprising: appending a last coordinate of the uncounted sub pixel subregion to the path, where the last coordinate comprises a current point; determining an edge of the pixel where the current point is located; navigating in the predetermined direction toward the next vertex; based on the navigating, determining if a starting point to a segment of another uncounted sub pixel subregion is on the edge before the next vertex; based on determining that no starting point is on the edge before the vertex, adding coordinates of the next vertex to the path and continuing the navigating in the predetermined direction toward the next vertex; and based on determining that there is a starting point to a segment of another uncounted sub pixel subregion on the edge before the vertex, navigating through the pixel along a segment to an intersection between a point of the contiguous points comprising the other uncounted sub pixel subregion and an edge of the pixel, adding the contiguous points to the path, marking the other uncounted sub pixel subregion as counted, and progressing from the intersection in the pre-determined direction to another vertex.

In some examples, the predetermined direction is selected from the group consisting of: clockwise and counterclockwise.

In some examples, the program code utilizing, the one or more sub pixel subregions to determine the combined area of sub pixel subregions comprises: the program code determining an area for each sub pixel subregion; and the program code adding each determined area together to generate the combined area of sub pixel subregions.

In some examples, the program code generates a pixel dictionary and updates the pixel dictionary to include the set of points, where a portion of the set of points comprises edge points.

In some examples, the program code generates a dictionary identifying edge pixels, where the generating comprises, for each pixel in the region of interest: the program code setting an internal area of the pixel to a constant; the program code determining if a center point of the pixel is within the region of interest; based on determining that the center of the pixel is within the region of interest, the program code determining if the center point is an edge point in the pixel dictionary; based on determining that the center point is the edge point, the program code determining if an edge area of the pixel is greater than zero; and the program code updating the pixel dictionary to include the pixel as an edge pixel.

In some examples, the constant is 1.

Figure 17:
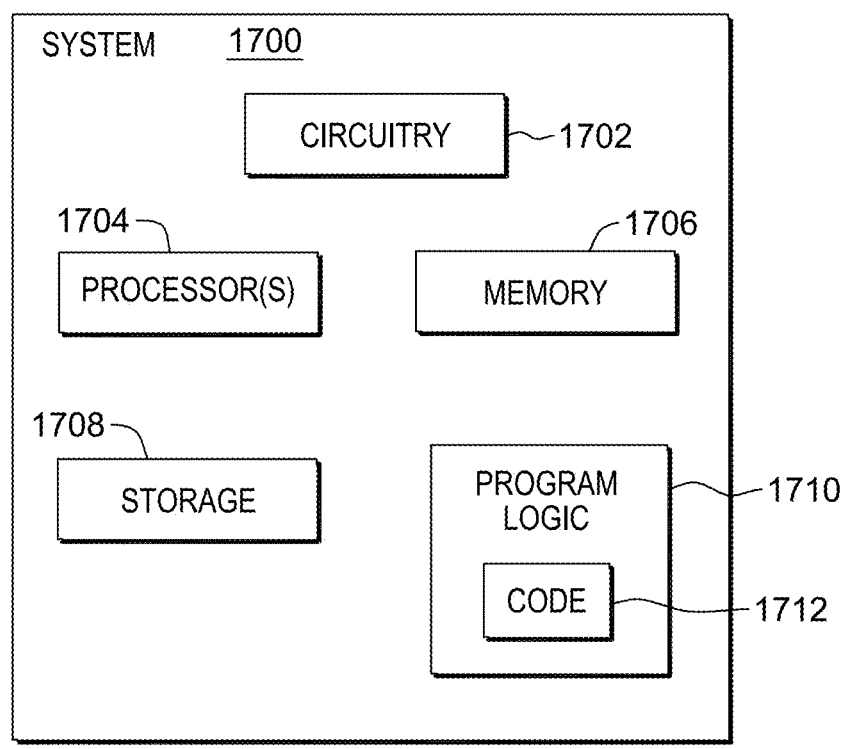
FIG. 17 depicts a computer system configured to perform an aspect of an embodiment of the present invention.

FIG. 17 illustrates a block diagram of a resource 1700 in computer system, such as, which is part of the technical architecture of certain embodiments of the technique. In FIG. 17, the resource 1700 may include a circuitry 1702 that may in certain embodiments include a microprocessor 1704. The computer system 1700 may also include a memory 1706 (e.g., a volatile memory device), and storage 1708. The storage 1708 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 1708 may comprise an internal storage device, an attached storage device and/or a network accessible storage device. The system 1700 may include a program logic 1710 including code 1712 that may be loaded into the memory 1706 and executed by the microprocessor 1704 or circuitry 1702. This resource 1700 can be a single resource in a cloud computing system. As such, the program code discussed herein can be provided as a service or installed to one or more users.

In certain embodiments, the program logic 1710 including code 1712 may be stored in the storage 1708, or memory 1706. In certain other embodiments, the program logic 1710 may be implemented in the circuitry 1702. Therefore, while FIG. 17 shows the program logic 1710 separately from the other elements, the program logic 1710 may be implemented in the memory 1706 and/or the circuitry 1702. The program logic 1710 may include the program code discussed in this disclosure that facilitates the reconfiguration of elements of various computer networks, including those in various figures.

Figure 18:
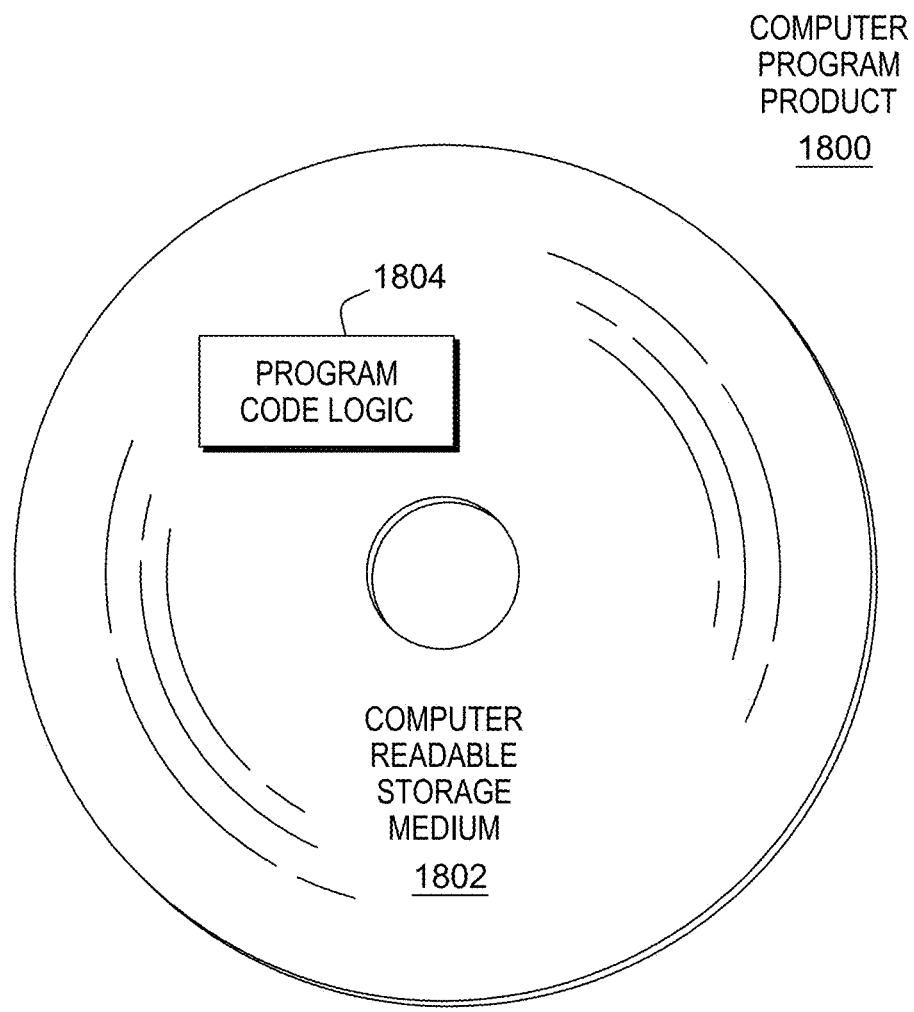
FIG. 18 depicts a computer program product incorporating one or more aspects of the present invention.

Using the processing resources of a resource 1700 to execute software, computer-readable code or instructions, does not limit where this code can be stored. Referring to FIG. 18, in one example, a computer program product 1800 includes, for instance, one or more non-transitory computer readable storage media 1802 to store computer readable program code means or logic 1804 thereon to provide and facilitate one or more aspects of the technique.

As will be appreciated by one skilled in the art, aspects of the technique may be embodied as a system, method or computer program product. Accordingly, aspects of the technique may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, aspects of the technique may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable signal medium may include a propagated data signal with computer readable program code embodied therein, for example, in baseband or as part of a carrier wave. Such a propagated signal may take any of a variety of forms, including, but not limited to, electro-magnetic, optical or any suitable combination thereof. A computer readable signal medium may be any computer readable medium that is not a computer readable storage medium and that can communicate, propagate, or transport a program for use by or in connection with an instruction execution system, apparatus or device.

A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Any combination of one or more computer readable medium(s) may be utilized. The computer readable medium may be a computer readable signal medium or a computer readable storage medium. A computer readable signal medium may include a propagated data signal with computer readable program code embodied therein, for example, in baseband or as part of a carrier wave. Such a propagated signal may take any of a variety of forms, including, but not limited to, electro-magnetic, optical or any suitable combination thereof. A computer readable signal medium may be any computer readable medium that is not a computer readable storage medium and that can communicate, propagate, or transport a program for use by or in connection with an instruction execution system, apparatus or device.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the technique may be written in any combination of one or more programming languages, including an object-oriented programming language, such as Java, Smalltalk, C++ or the like, and conventional procedural programming languages, such as the "C" programming language, PHP, ASP, assembler or similar programming languages, as well as functional programming languages and languages for technical computing (e.g., Matlab). The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). Furthermore, more than one computer can be used for implementing the program code, including, but not limited to, one or more resources in a cloud computing environment.

Aspects of the technique are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions, also referred to as software and/or program code, may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the technique. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In addition to the above, one or more aspects of the technique may be provided, offered, deployed, managed, serviced, etc. by a service provider who offers management of customer environments. For instance, the service provider can create, maintain, support, etc. computer code and/or a computer infrastructure that performs one or more aspects of the technique for one or more customers. In return, the service provider may receive payment from the customer under a subscription and/or fee agreement, as examples. Additionally, or alternatively, the service provider may receive payment from the sale of advertising content to one or more third parties.

In one aspect of the technique, an application may be deployed for performing one or more aspects of the technique. As one example, the deploying of an application comprises providing computer infrastructure operable to perform one or more aspects of the technique.

As a further aspect of the technique, a computing infrastructure may be deployed comprising integrating computer readable code into a computing system, in which the code in combination with the computing system is capable of performing one or more aspects of the technique.

As yet a further aspect of the technique, a process for integrating computing infrastructure comprising integrating computer readable code into a computer system may be provided. The computer system comprises a computer readable medium, in which the computer medium comprises one or more aspects of the technique. The code in combination with the computer system is capable of performing one or more aspects of the technique.

Further, other types of computing environments can benefit from one or more aspects of the technique. As an example, an environment may include an emulator (e.g., software or other emulation mechanisms), in which a particular architecture (including, for instance, instruction execution, architected functions, such as address translation, and architected registers) or a subset thereof is emulated (e.g., on a native computer system having a processor and memory). In such an environment, one or more emulation functions of the emulator can implement one or more aspects of the technique, even though a computer executing the emulator may have a different architecture than the capabilities being emulated. As one example, in emulation mode, the specific instruction or operation being emulated is decoded, and an appropriate emulation function is built to implement the individual instruction or operation.

In an emulation environment, a host computer includes, for instance, a memory to store instructions and data; an instruction fetch unit to fetch instructions from memory and to optionally, provide local buffering for the fetched instruction; an instruction decode unit to receive the fetched instructions and to determine the type of instructions that have been fetched; and an instruction execution unit to execute the instructions. Execution may include loading data into a register from memory; storing data back to memory from a register; or performing some type of arithmetic or logical operation, as determined by the decode unit. In one example, each unit is implemented in software. For instance, the operations being performed by the units are implemented as one or more subroutines within emulator software.

Further, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or steps plus function elements in the descriptions below, if any, are intended to include any structure, material, or act for performing the function in combination with other elements as specifically noted. The description of the technique has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular uses contemplated.

The invention claimed is:

1. A computer-implemented method, comprising:
obtaining, by one or more processors, input data comprising an image and image data comprising coordinates defining a region of interest in the image, wherein each coordinate defines a point on the image, wherein the image comprises pixels;
determining, by the one or more processors, a sequential order for navigating the coordinates defining the region of interest, wherein the sequential order is non-duplicative of any coordinate of the coordinates;
defining, by the one or more processors, a set of points comprising a border around the region of interest, wherein the defining comprises supplementing the coordinates comprising points in the image by adding additional points comprising intersection points, wherein each intersection point is an intersection of a line between two coordinates of the coordinates with an edge of a pixel of pixels in the image, wherein the coordinates comprising points and the intersection points comprise the set of points;
determining, by the one or more processors, a combined area of sub pixel subregions in each pixel comprising one or more points in the set of points, the determining comprising:
identifying, by the one or more processors, one or more points of the set of points on the pixel;
generating, by the one or more processors, based on the one or more points, one or more sub pixel subregions, wherein each sub pixel subregion comprises contiguous points of the set of points, wherein the contiguous points are within or on the pixel; and
utilizing, by the one or more processors, the one or more sub pixel subregions to determine the combined area of sub pixel subregions.

2. The computer-implemented method of claim 1, further comprising:
based on the determining the combined area of sub pixel subregions in each pixel, identifying, by the one or more processors, pixels internal the sub pixel subregions.

3. The computer-implemented method of claim 2, further comprising:
generating, by the one or more processors, based on determining the combined area of sub pixel subregions in each pixel and the one or more sub pixel subregions of each pixel, a dictionary identifying edge pixels and a percent of each edge pixel of the edge pixels within the region of interest.

4. The computer-implemented method of claim 2, further comprising:
generating, by the one or more processors, based on determining the combined area of sub pixel subregions in each pixel and the one or more sub pixel subregions of each pixel, a dictionary comprising a list of the pixels internal to the regions, wherein the pixels internal to the regions are internal to the regions of interest.

5. The computer-implemented method of claim 1, wherein the image is a Digital Imaging and Communications in Medicine (DICOM) image.

6. The computer-implemented method of claim 1, wherein the sequential order is selected from the group consisting of: clockwise and counterclockwise.

7. The computer-implemented method of claim 1, wherein utilizing the one or more sub pixel subregions to determine the combined area of sub pixel subregions for each pixel comprises:
generating, by the one or more processors, one or more paths, based on navigating along each edge of the pixel, starting with the edge where a current point is located, in a pre-determined direction, toward a next vertex of the pixel, until each sub pixel subregion is counted, the navigating comprises:
determining, by the one or more processors, if any of the sub pixel subregions are uncounted;
based on determining that at least one sub pixel subregion is uncounted, generating a path comprising contiguous points comprising the at least one sub pixel subregion, the generating comprising:
appending, by the one or more processors, a last coordinate of the uncounted sub pixel subregion to the path, where the last coordinate comprises a current point;
determining, by the one or more processors, an edge of the pixel where the current point is located;
navigating, by the one or more processors, in the predetermined direction toward the next vertex;

based on the navigating, determining, by the one or more processors, if a starting point to a segment of another uncounted sub pixel subregion is on the edge before the next vertex;

based on determining that no starting point is on the edge before the vertex, adding coordinates of the next vertex to the path and continuing the navigating in the predetermined direction toward the next vertex; and based on determining that there is a starting point to a segment of another uncounted sub pixel subregion on the edge before the vertex, navigating through the pixel along a segment to an intersection between a point of the contiguous points comprising the other uncounted sub pixel subregion and an edge of the pixel, adding the contiguous points to the path, marking the other uncounted sub pixel subregion as counted, and progressing from the intersection in the pre-determined direction to another vertex.

8. The computer-implemented method of claim 7, wherein the predetermined direction is selected from the group consisting of: clockwise and counterclockwise.

9. The computer-implemented method of claim 1, wherein utilizing, the one or more sub pixel subregions to determine the combined area of sub pixel subregions comprises:
  determining, by the one or more processors, an area for each sub pixel subregion; and
  adding, by the one or more processors, each determined area together to generate the combined area of sub pixel subregions.

10. The computer-implemented method of claim 9, further comprising:
  generating, by the one or more processors, a pixel dictionary; and
  updating, by the one or more processors, the pixel dictionary to include the set of points, wherein a portion of the set of points comprises edge points.

11. The computer-implemented method of claim 10, further comprising:
  generating, by the one or more processors, a dictionary identifying edge pixels, wherein the generating comprises, for each pixel in the region of interest:
    setting, by the one or more processors, an internal area of the pixel to a constant;
    determining, by the one or more processors, if a center point of the pixel is within the region of interest;
    based on determining that the center of the pixel is within the region of interest, determining, by the one or more processors, if the center point is an edge point in the pixel dictionary;
    based on determining that the center point is the edge point, determining, by the one or more processors, if an edge area of the pixel is greater than zero; and
    updating, by the one or more processors, the pixel dictionary to include the pixel as an edge pixel.

12. The computer-implemented method of claim 1, wherein the constant is 1.

13. A computer program product comprising:
  a non-transitory computer readable storage medium readable by one or more processors and storing instructions for execution by the one or more processors for performing a method comprising:
    obtaining, by the one or more processors, input data comprising an image and image data comprising coordinates defining a region of interest in the image, wherein each coordinate defines a point on the image, wherein the image comprises pixels;
    determining, by the one or more processors, a sequential order for navigating the coordinates defining the region of interest, wherein the sequential order is non-duplicative of any coordinate of the coordinates;
    defining, by the one or more processors, a set of points comprising a border around the region of interest, wherein the defining comprises supplementing the coordinates comprising points in the image by adding additional points comprising intersection points, wherein each intersection point is an intersection of a line between two coordinates of the coordinates with an edge of a pixel of pixels in the image, wherein the coordinates comprising points and the intersection points comprise the set of points;
    determining, by the one or more processors, a combined area of sub pixel subregions in each pixel comprising one or more points in the set of points, the determining comprising:
      identifying, by the one or more processors, one or more points of the set of points on the pixel;
      generating, by the one or more processors, based on the one or more points, one or more sub pixel subregions, wherein each sub pixel subregion comprises contiguous points of the set of points, wherein the contiguous points are within or on the pixel; and
      utilizing, by the one or more processors, the one or more sub pixel subregions to determine the combined area of sub pixel subregions.

14. The computer program product of claim 13, the method further comprising:
  based on the determining the combined area of sub pixel subregions in each pixel, identifying, by the one or more processors, pixels internal the sub pixel subregions.

15. The computer program product of claim 14, the method further comprising:
  generating, by the one or more processors, based on determining the combined area of sub pixel subregions in each pixel and the one or more sub pixel subregions of each pixel, a dictionary identifying edge pixels and a percent of each edge pixel of the edge pixels within the region of interest.

16. The computer program product of claim 14, further comprising:
  generating, by the one or more processors, based on determining the combined area of sub pixel subregions in each pixel and the one or more sub pixel subregions of each pixel, a dictionary comprising a list of the pixels internal to the regions, wherein the pixels internal to the regions are internal to the regions of interest.

17. The computer program product of claim 13, wherein the image is a Digital Imaging and Communications in Medicine (DICOM) image.

18. The computer program product of claim 13, wherein the sequential order is selected from the group consisting of: clockwise and counterclockwise.

19. The computer program product of claim 13, wherein utilizing the one or more sub pixel subregions to determine the combined area of sub pixel subregions for each pixel comprises:
  generating, by the one or more processors, one or more paths, based on navigating along each edge of the pixel, starting with the edge where a current point is located, in a pre-determined direction, toward a next vertex of the pixel, until each sub pixel subregion is counted, the navigating comprises:

determining, by the one or more processors, if any of the sub pixel subregions are uncounted;

based on determining that at least one sub pixel subregion is uncounted, generating a path comprising contiguous points comprising the at least one sub pixel subregion, the generating comprising:

appending, by the one or more processors, a last coordinate of the uncounted sub pixel subregion to the path, where the last coordinate comprises a current point;

determining, by the one or more processors, an edge of the pixel where the current point is located;

navigating, by the one or more processors, in the predetermined direction toward the next vertex;

based on the navigating, determining, by the one or more processors, if a starting point to a segment of another uncounted sub pixel subregion is on the edge before the next vertex;

based on determining that no starting point is on the edge before the vertex, adding coordinates of the next vertex to the path and continuing the navigating in the predetermined direction toward the next vertex; and based on determining that there is a starting point to a segment of another uncounted sub pixel subregion on the edge before the vertex, navigating through the pixel along a segment to an intersection between a point of the contiguous points comprising the other uncounted sub pixel subregion and an edge of the pixel, adding the contiguous points to the path, marking the other uncounted sub pixel subregion as counted, and progressing from the intersection in the pre-determined direction to another vertex.

20. A system comprising:
a memory;
one or more processors in communication with the memory;
program instructions executable by the one or more processors via the memory to perform a method, the method comprising:

obtaining, by the one or more processors, input data comprising an image and image data comprising coordinates defining a region of interest in the image, wherein each coordinate defines a point on the image, wherein the image comprises pixels;

determining, by the one or more processors, a sequential order for navigating the coordinates defining the region of interest, wherein the sequential order is non-duplicative of any coordinate of the coordinates;

defining, by the one or more processors, a set of points comprising a border around the region of interest, wherein the defining comprises supplementing the coordinates comprising points in the image by adding additional points comprising intersection points, wherein each intersection point is an intersection of a line between two coordinates of the coordinates with an edge of a pixel of pixels in the image, wherein the coordinates comprising points and the intersection points comprise the set of points;

determining, by the one or more processors, a combined area of sub pixel subregions in each pixel comprising one or more points in the set of points, the determining comprising:

identifying, by the one or more processors, one or more points of the set of points on the pixel;

generating, by the one or more processors, based on the one or more points, one or more sub pixel subregions, wherein each sub pixel subregion comprises contiguous points of the set of points, wherein the contiguous points are within or on the pixel; and utilizing, by the one or more processors, the one or more sub pixel subregions to determine the combined area of sub pixel subregions.

* * * * *